(12) United States Patent
Koser

(10) Patent No.: US 10,302,634 B2
(45) Date of Patent: May 28, 2019

(54) TUNABLE AFFINITY SYSTEM AND METHOD FOR FERROFLUID-BASED CAPTURE ASSAYS

(71) Applicant: Ancera, LLC, Branford, CT (US)

(72) Inventor: Hur Koser, Wallingford, CT (US)

(73) Assignee: ANCERA, LLC, Branford, CT (US)

( * ) Notice: Subject to any disclaimer, the term of this patent is extended or adjusted under 35 U.S.C. 154(b) by 0 days.

(21) Appl. No.: 15/740,288

(22) PCT Filed: Jul. 1, 2016

(86) PCT No.: PCT/US2016/040861
§ 371 (c)(1),
(2) Date: Dec. 27, 2017

(87) PCT Pub. No.: WO2017/004595
PCT Pub. Date: Jan. 5, 2017

(65) Prior Publication Data
US 2018/0188246 A1 Jul. 5, 2018

Related U.S. Application Data

(60) Provisional application No. 62/187,521, filed on Jul. 1, 2015.

(51) Int. Cl.
*G01N 33/543* (2006.01)
*B03C 1/32* (2006.01)
(Continued)

(52) U.S. Cl.
CPC ....... *G01N 33/54333* (2013.01); *B03C 1/023* (2013.01); *B03C 1/0332* (2013.01);
(Continued)

(58) Field of Classification Search
CPC .............. G01N 33/54333; B03C 1/288; B03C 1/0332; B03C 1/023; B03C 1/0335; B03C 1/32
See application file for complete search history.

(56) References Cited

U.S. PATENT DOCUMENTS

| 2003/0203507 A1 | 10/2003 | Liberti et al. |
| 2008/0038725 A1* | 2/2008 | Luo ........................ C12Q 1/682 435/6.16 |

(Continued)

FOREIGN PATENT DOCUMENTS

WO   2014145765 A1   9/2014

OTHER PUBLICATIONS

International Search Report and Written Opinion for International Patent Application No. PCT/US2016/040861, dated Sep. 13, 2016.

*Primary Examiner* — Melanie Brown
(74) *Attorney, Agent, or Firm* — Cooley LLP

(57) ABSTRACT

Devices, methods, and systems are provided for extracting particles from a ferrofluid and for rapid affinity measurements. Such systems may comprise a fluidic channel or chamber configured to include a ferrofluid having a plurality of target particles and background particles. The systems may include a capture region configured to capture at least a portion of the plurality of target particles. In addition, the systems include a first magnetic field generator and a second magnetic field generator. The first magnetic field generator may be arranged proximate to the fluidic channel, the first magnetic field generator being configured to generate a first magnetic field configured to direct the plurality of target particles towards the capture region. The second magnetic field generator can be arranged to be proximate to the capture region, and is further configured to generate an affinity thresholding magnetic field configured to remove background particles from the capture region.

21 Claims, 16 Drawing Sheets

(51) Int. Cl.
*B03C 1/023* (2006.01)
*B03C 1/033* (2006.01)
*B03C 1/28* (2006.01)

(52) U.S. Cl.
CPC ............ *B03C 1/0335* (2013.01); *B03C 1/288* (2013.01); *B03C 1/32* (2013.01); *B03C 2201/18* (2013.01); *B03C 2201/26* (2013.01)

(56) References Cited

U.S. PATENT DOCUMENTS

| | | | |
|---|---|---|---|
| 2009/0251136 A1* | 10/2009 | Prins | B82Y 25/00 |
| | | | 324/228 |
| 2010/0093052 A1 | 4/2010 | Chalmers et al. | |
| 2011/0065209 A1* | 3/2011 | Heil | G01N 33/54326 |
| | | | 436/501 |
| 2012/0080360 A1 | 4/2012 | Stone et al. | |
| 2012/0237997 A1 | 9/2012 | Koser | |

* cited by examiner

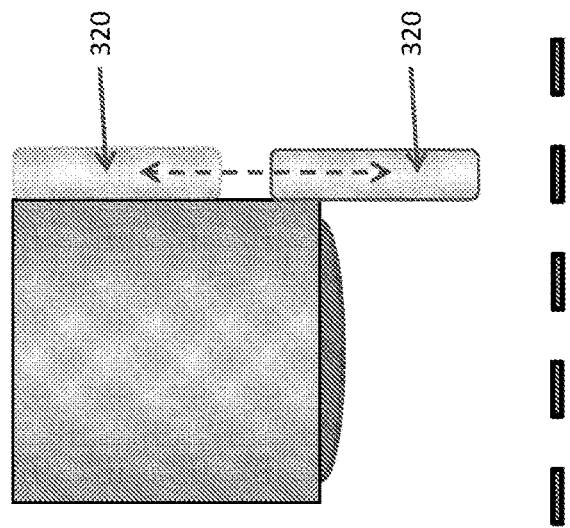
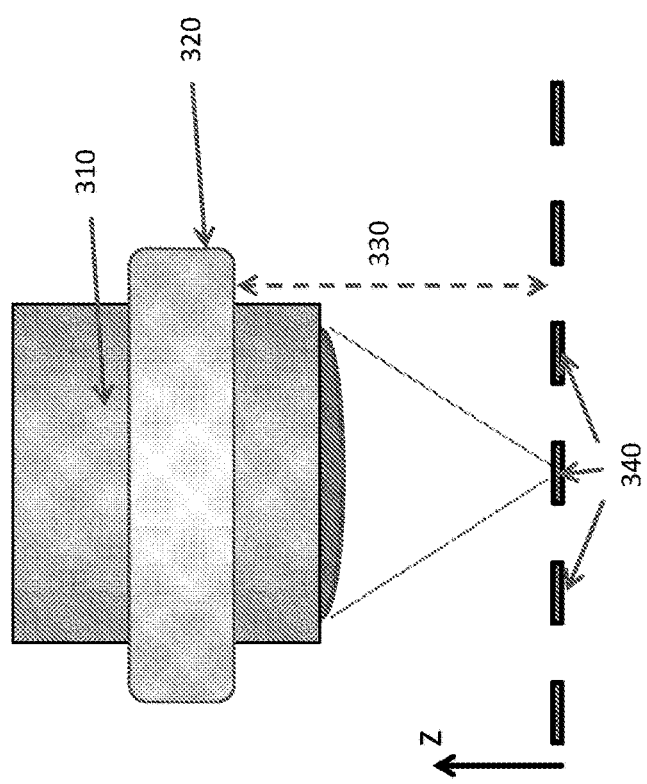
FIGURE 3B
FIGURE 3A

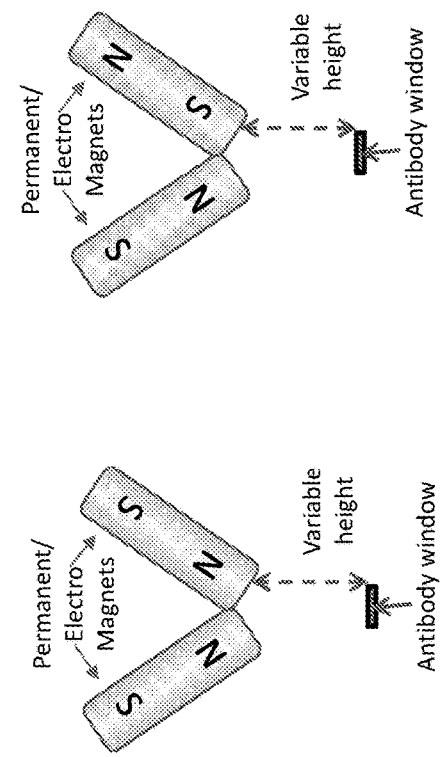
FIGURE 4A
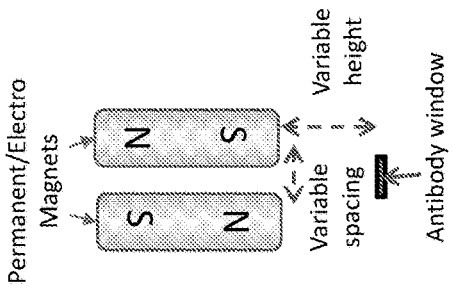
FIGURE 4B
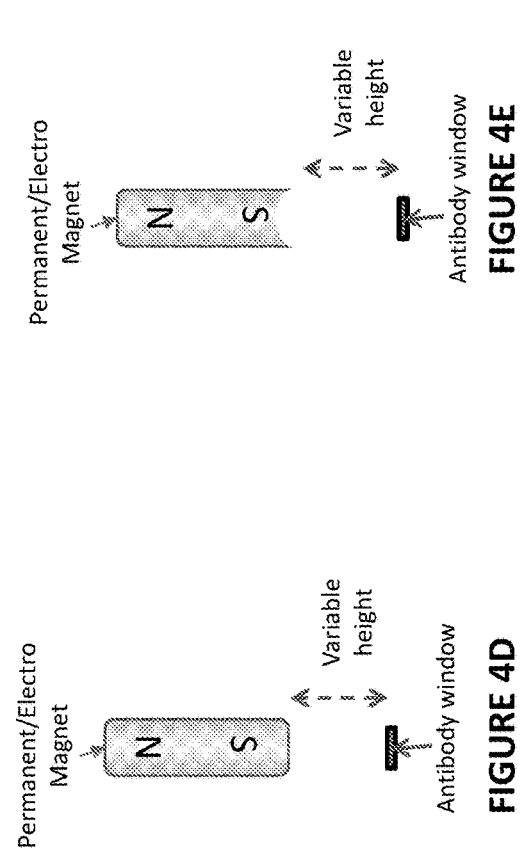
FIGURE 4C
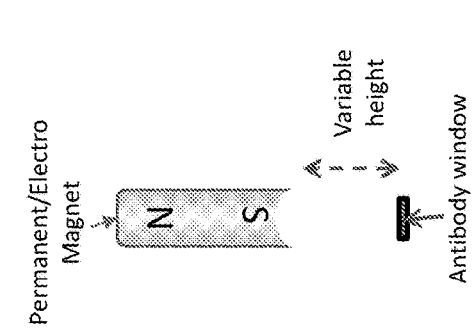
FIGURE 4D
FIGURE 4E

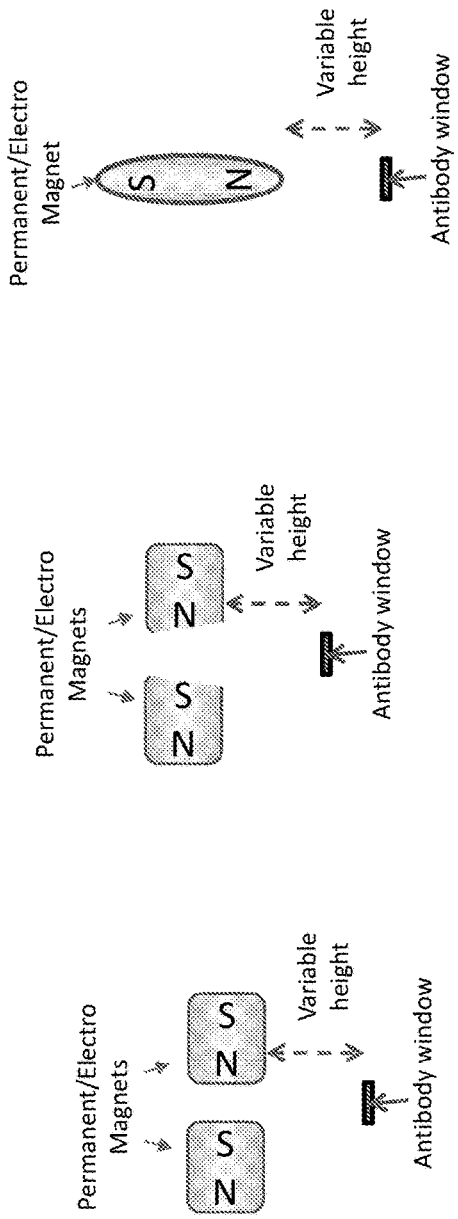
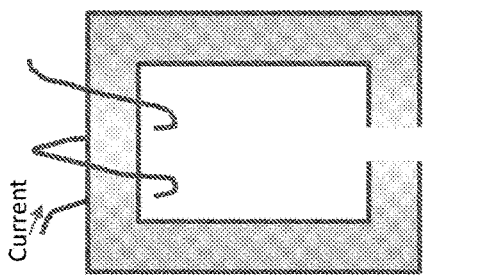
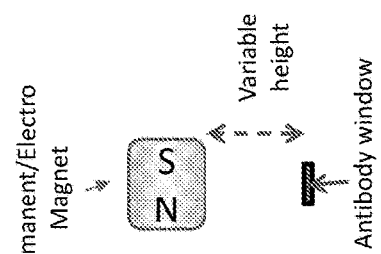
FIGURE 4F, FIGURE 4G, FIGURE 4H, FIGURE 4I, FIGURE 4J

TUNABLE AFFINITY SYSTEM AND METHOD FOR FERROFLUID-BASED CAPTURE ASSAYS

CROSS-REFERENCE TO RELATED APPLICATIONS

This application is a national stage application of and claims priority to International Patent Application No. PCT/US2016/040861, filed Jul. 1, 2016, and entitled "Tunable Affinity System and Method for Ferrofluid-Based Capture Assays," which in turn claims priority to U.S. Provisional Patent Application No. 62/187,521, filed Jul. 1, 2015, and entitled "A Tunable Affinity System and Method for Ferrofluid-Based Capture Assays". The present application incorporates herein by reference the disclosures of each of the above-referenced applications in their entireties.

FIELD OF THE INVENTION

The present disclosure relates to methods and systems for extracting particles from ferrofluids and removing background particles from capture regions of assays. It further relates to rapid affinity measurements between receptors immobilized on an assay surface and ligands expressed and/or presented on the surface of cells and/or beads.

BACKGROUND

WO2011/071912, WO2012/057878, and WO2014/144782 present systems and methods for separating microparticles or cells within a ferrofluid medium using magnetic forces. Magnetic field excitations can sort, separate, focus, and even capture cells and other microparticles.

Mechanical exclusion, via well-known filtration is, by its very nature, prone to clogging, and also subsequent increases in pressure drop across the filter as the filter becomes more and more clogged. Such filtration means rely on physically stopping a large enough target particle across a smaller opening on a surface. Additionally, diffusion on traditional assays is slowed by speed limitations. For example, in traditional immunoassays, multiple time-consuming and labor-intensive wash cycles are required between steps.

SUMMARY OF SOME OF THE EMBODIMENTS

Some embodiments of this disclosure present systems, methods and devices which remove background particles from a capture region of an assay.

Some embodiments of this disclosure present one or more additional features and/or functionality to methods, systems and devices presented in previous disclosures including, for example, PCT Publication Nos. WO2011/071912, WO2012/057878, and WO2014/144782, all of which are herein incorporated by reference in their entireties.

In some embodiments, devices, methods, and systems are provided for extracting particles from a ferrofluid and for rapid affinity measurements. Such embodiments may comprise a fluidic channel or chamber, a capture region, and a first and a second magnetic field generators. The fluidic channel or chamber may be configured to include a ferrofluid having a plurality of target particles and background particles. In some embodiments, the fluidic channel is configured to receive a flow of the ferrofluid flow. Further, the capture region may be located along a first side of the fluidic channel functionalized with a plurality of receptor particles configured to capture at least a portion of the plurality of target particles. The first magnetic field generator can be arranged proximate to the fluidic channel, the first magnetic field generator being configured to generate a first magnetic field that is configured to direct the plurality of target particles towards the capture region. In addition, the second magnetic field generator may be arranged proximate to the capture region, the second magnetic field generator being configured to generate an affinity thresholding magnetic field configured to remove background particles from the capture region. Further, the embodiments may include a detector configured to detect the at least a portion of the plurality of target particles captured by the plurality of receptor particles. The plurality of target particles comprise cells, including one or more of bacteria, blood cells, and eukaryotic cells. In some embodiments, the plurality of target particles include non-magnetic microbeads.

In some embodiments, the detector may include one or more of an automated scanning microscope, a sensitive mass balance, an electrochemical sensor, an electroimpedance sensor and/or a magnetic sensor. In some embodiments, the disclosed embodiments include an outlet configured to collect the released target particles for storing and/or further processing.

In some embodiments, the affinity thresholding magnetic field may be configured to remove background particles which are captured by at least a portion of the plurality of receptor particles. The capture region may include a plurality of capture regions, each capture region functionalized with a plurality of receptor particles configured to capture same type of target particles. In some embodiments, the capture region includes a plurality of capture regions, a first capture region functionalized with a plurality of receptor particles configured to capture a different type of target particle than a second capture region of the plurality of capture regions.

In some embodiments, the first magnetic field generator includes electrodes running along at least a section of a second side of the fluidic channel, the second side being opposite to the first side. The second magnetic field generator can include a permanent magnet and/or an electromagnet. Further, the second magnetic field generator can include an electromagnet, and a strength of the affinity thresholding magnetic field is controlled by varying an amplitude of an excitation current of the electromagnet. In addition, the second magnetic field generator can include a permanent magnet, and a strength of the affinity thresholding magnetic field is controlled by varying a separation distance between the second magnetic field generator and the fluidic channel is adjustable. In some embodiments, the magnitude of the gradient of an affinity thresholding force corresponding to the affinity thresholding magnetic field along a separation distance separating the second magnetic field generator from the fluidic channel can be less than a threshold gradient value.

In some embodiments, the capture region may include at least a first capture region and a neighboring second capture region, and a spacing between the first capture region and the second capture region is configured so as to reduce a magnitude of stray magnetic fields on the first capture region below a minimum stray threshold when the second magnetic field generator is interrogating the second capture region.

In some embodiments, the force applied by the affinity thresholding magnetic field on the at least a portion of the plurality of target particles captured by the plurality of receptor particles is less than an affinity bond strength of a target particle to a receptor particle. In some embodiments, the affinity thresholding magnetic field is further configured such that after the removal of the background particles from the capture region, a force applied by the affinity thresholding magnetic field on captured target particles breaks an affinity bond strength between the captured target particles and corresponding receptor particles to release the captured target particles.

In some embodiments, a method comprising the steps of receiving or otherwise providing a ferrofluid having a plurality of target particles and background particles in a fluidic channel or chamber; generating, by a first magnetic field generator, a first magnetic field configured to direct at least a portion of the plurality of target particles towards a capture region located along a first side of the fluidic channel, the capture region functionalized with a plurality of receptor particles configured to capture the plurality of target particles; and generating an affinity thresholding magnetic field configured to remove background particles from the capture region are disclosed. In some embodiments, the receiving/providing step comprises receiving/providing a flow of the ferrofluid. In some embodiments, the steps further include detecting target particles captured by a second portion of the plurality of receptor particles.

In some embodiments, the affinity thresholding magnetic field is configured to remove background particles captured by at least a first portion of the plurality of receptor particles. The affinity thresholding magnetic field is further configured to break an affinity bond strength between captured target particles and corresponding capturing receptor particles after removing the background particles from the capture region.

In some embodiments, a method comprising the steps of receiving or otherwise providing a ferrofluid configured to receive and/or contain a plurality of target particles in a fluidic channel or chamber; generating, by a first magnetic field generator, a first magnetic field configured to direct at least a portion of the plurality of target particles towards a capture region located along a first side of the fluidic channel or chamber, the capture region functionalized with a plurality of receptor particles configured to capture the plurality of target particles; generating an affinity thresholding magnetic field configured to remove target particles captured by the plurality of receptor particles in the capture region, the second magnetic field generator arranged proximate to the fluidic channel; and detecting a remaining amount of captured target particles after an application of the affinity thresholding magnetic field to remove the captured target particles from the capture region is disclosed. In some embodiments, the receiving/providing step comprises receiving/providing a flow of the ferrofluid. Further, the method includes the step of detecting a remaining amount of captured target particles after an application of the affinity thresholding magnetic field to remove the captured target particles. Determining an affinity bond strength may also include determining the remaining amount of captured target particles is less than a predetermined threshold value. The method also includes the step of determining, based on the remaining amount, an affinity bond strength between a target particle and a receptor particle. In some embodiments, the affinity thresholding magnetic field is configured to remove target particles captured by the plurality of receptor particles in the capture region.

In some embodiments, a plurality of unbound (or non-specifically bound) particles may also collect in the capture region. A second magnetic field may then be generated, using an electromagnet and/or a permanent magnet, and applied adjacent to the capture region, at a predetermined orientation relative thereto. The second magnetic field, which may be understood as an affinity thresholding magnetic field, may be tuned to remove the weakly and non-specifically adhered particles (henceforth referred to as background particles) from the capture region without removing the strongly and specifically bound particles (henceforth referred to as target particles) from the capture region. Alternatively, the affinity thresholding magnetic field may be tuned to remove a majority of the background particles that are adhered to the capture region while removing only a small minority of target particles. Thus, in some embodiments, the ratio of target particles that remain on the capture region to background particles that remain on the capture region (i.e., the signal-to-noise ratio of the assay) is higher after the affinity thresholding magnetic field is applied, compared to the ratio of target to background particles before the application of the affinity thresholding magnetic field. A detector may be used to detect the target particles that are bound to the capture region. The detector may be an automated scanning microscope, a sensitive mass balance, an electrical impedance sensor, a magnetic sensor or an electrochemical sensor.

BRIEF DESCRIPTION OF SOME OF THE EMBODIMENTS

Figure 3C:
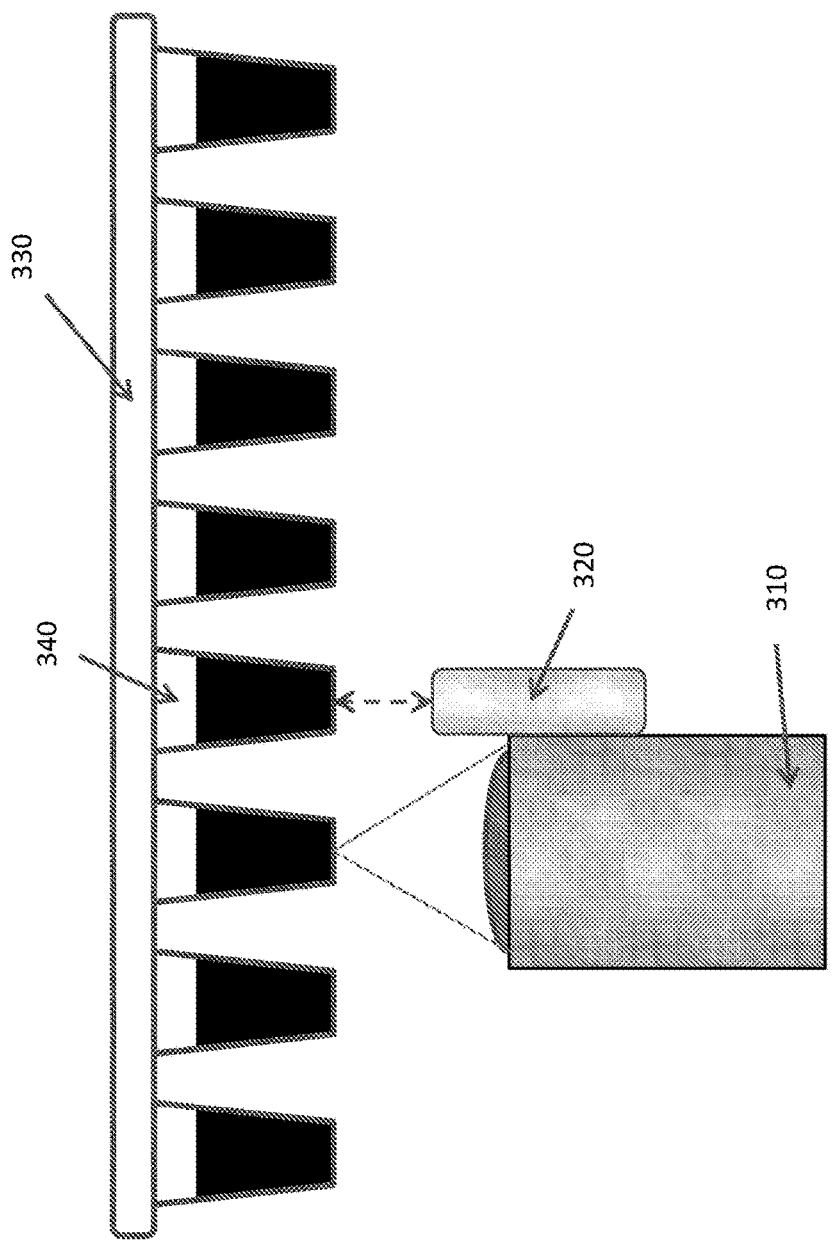

FIGS. 3A-C show schematics of an optical scanner and a magnetic structure configured for respectively monitoring and manipulating particles within a ferrofluid, according to some embodiments.

FIGS. 4A-J show several magnetic structure arrangements configured for manipulating particles within a ferrofluid, according to some embodiments.

Figure 5A:
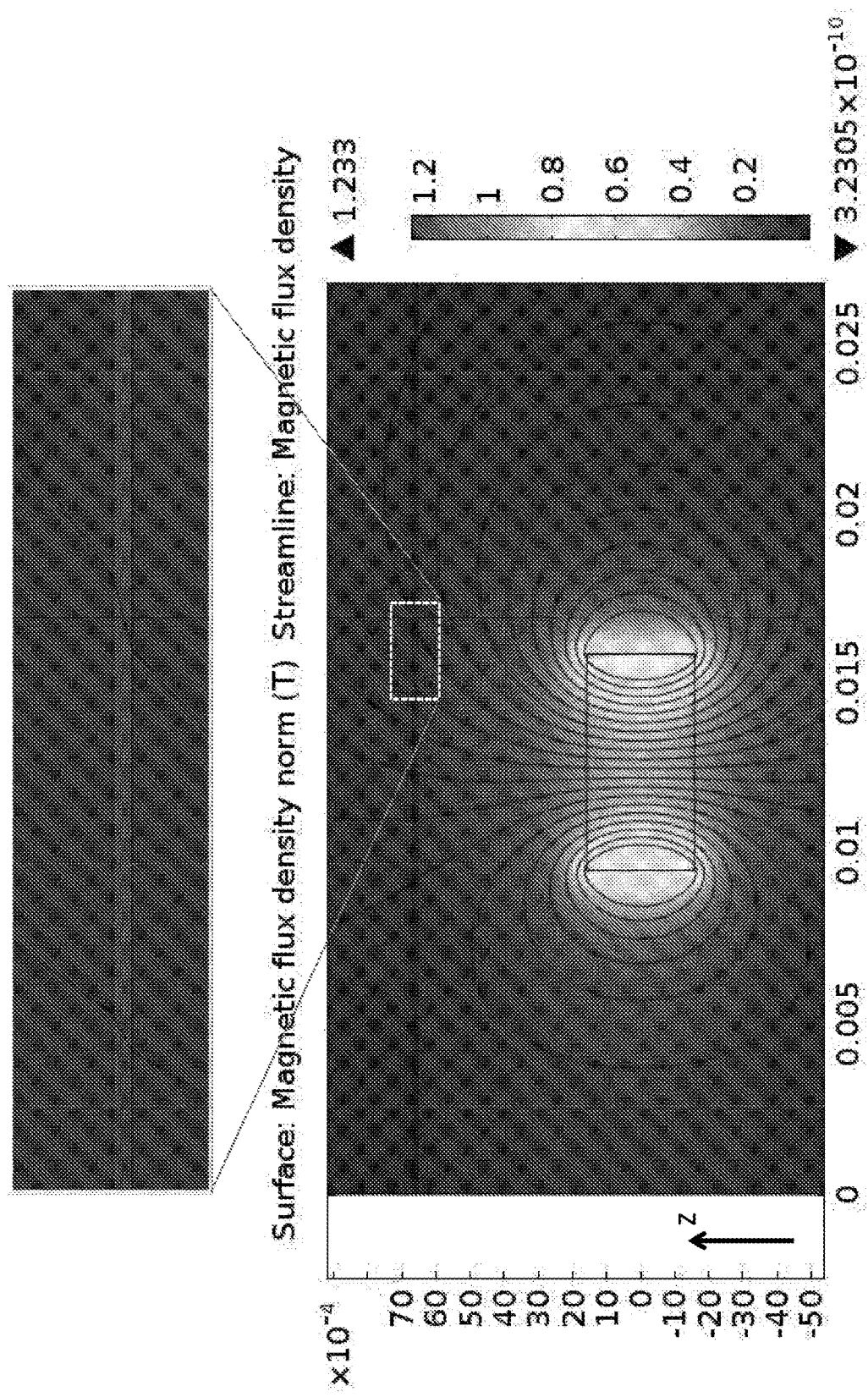

FIG. 5A shows an example magnetic flux density distribution of a magnetic structure configured for manipulating particles within a ferrofluid, according to some embodiments.

Figure 5C:
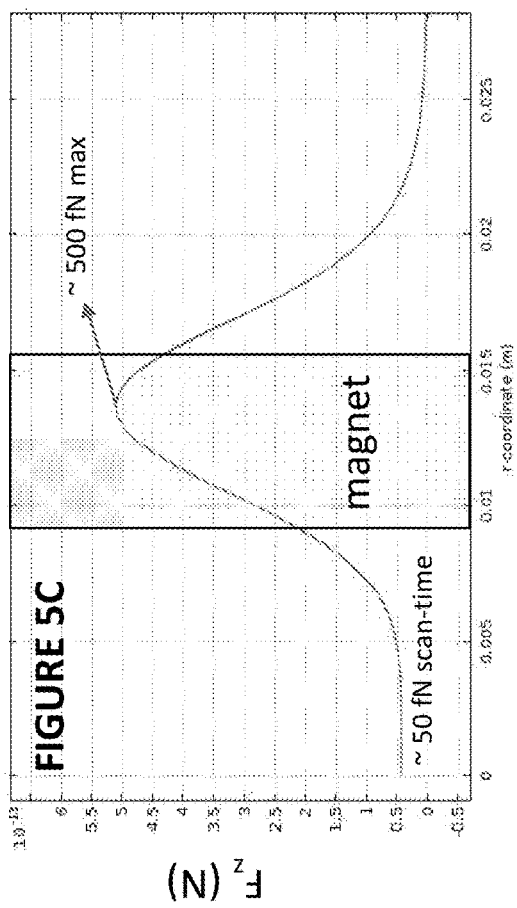
Figure 5D:
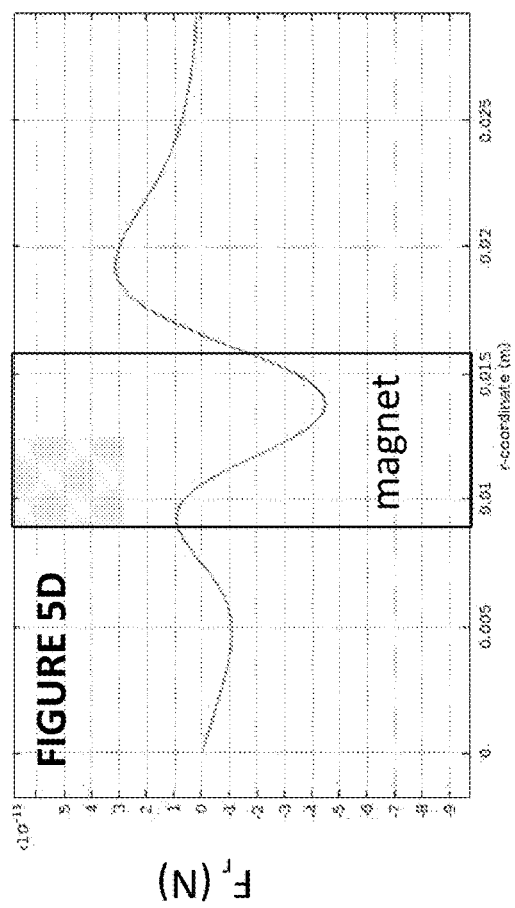
Figure 5B:
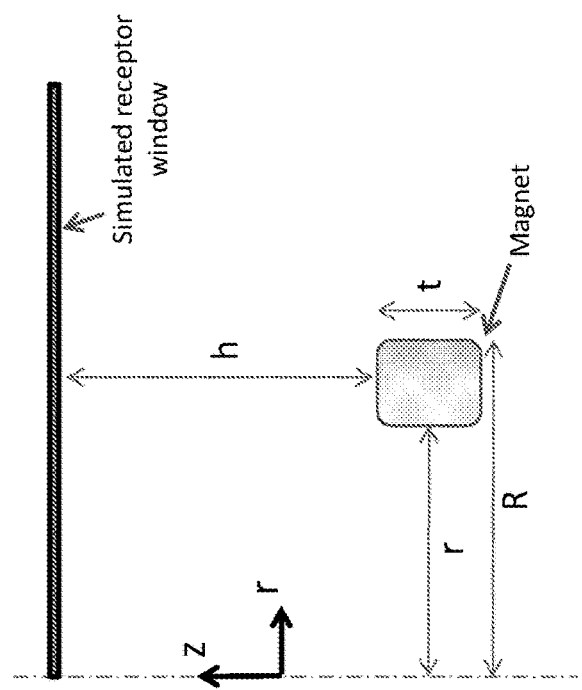
Figure 6A:
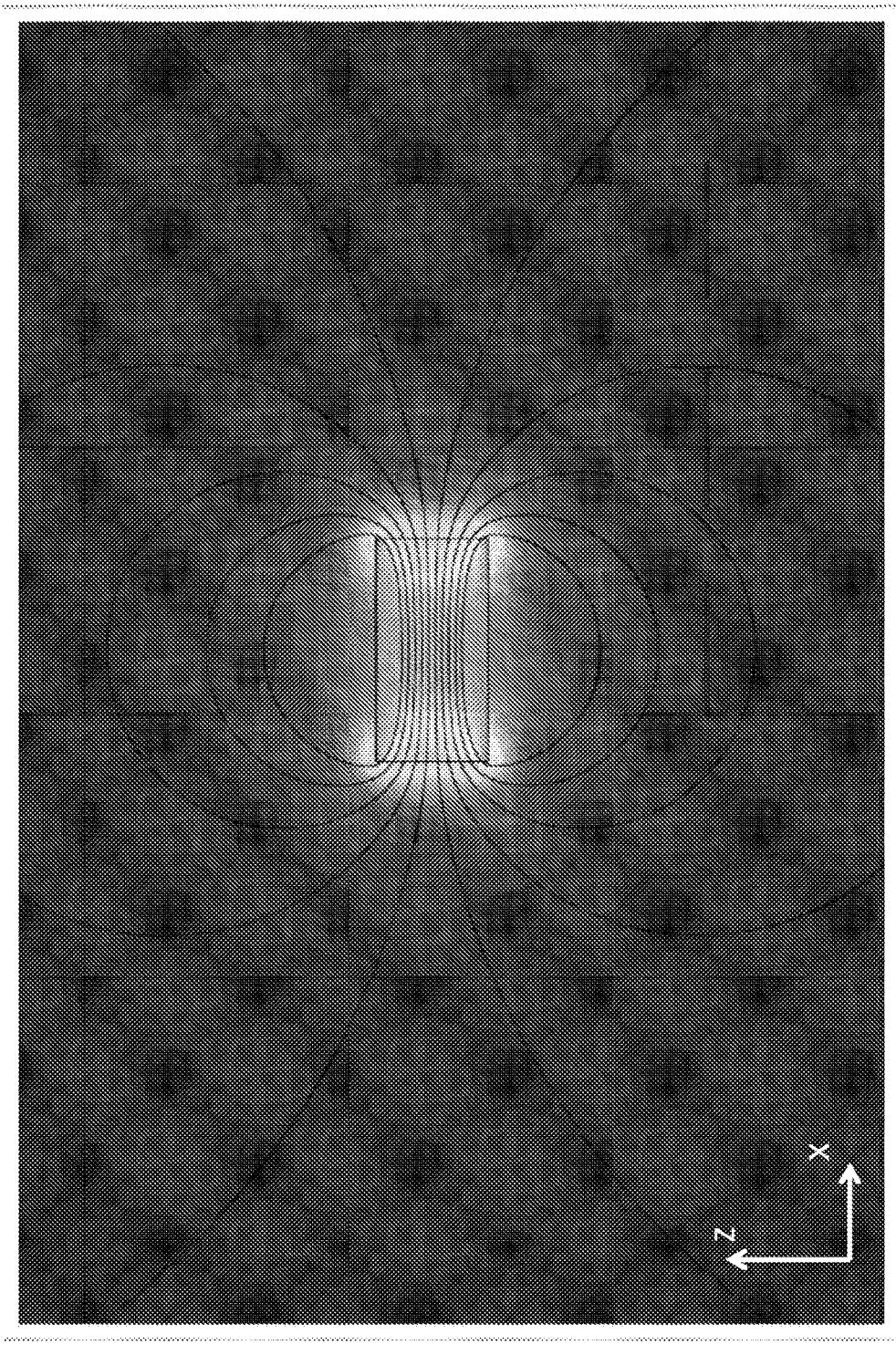
Figure 6B:
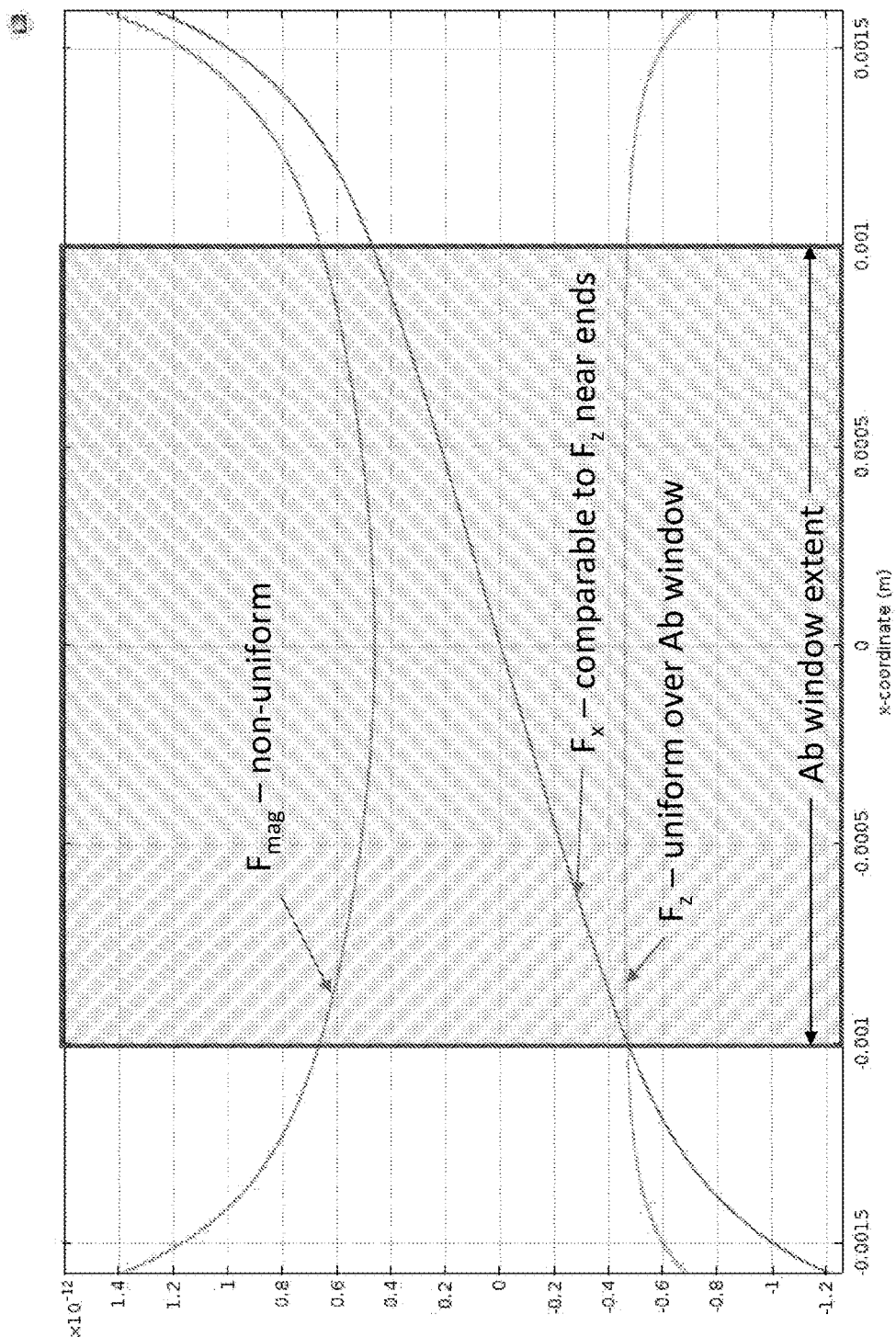
Figure 7A:
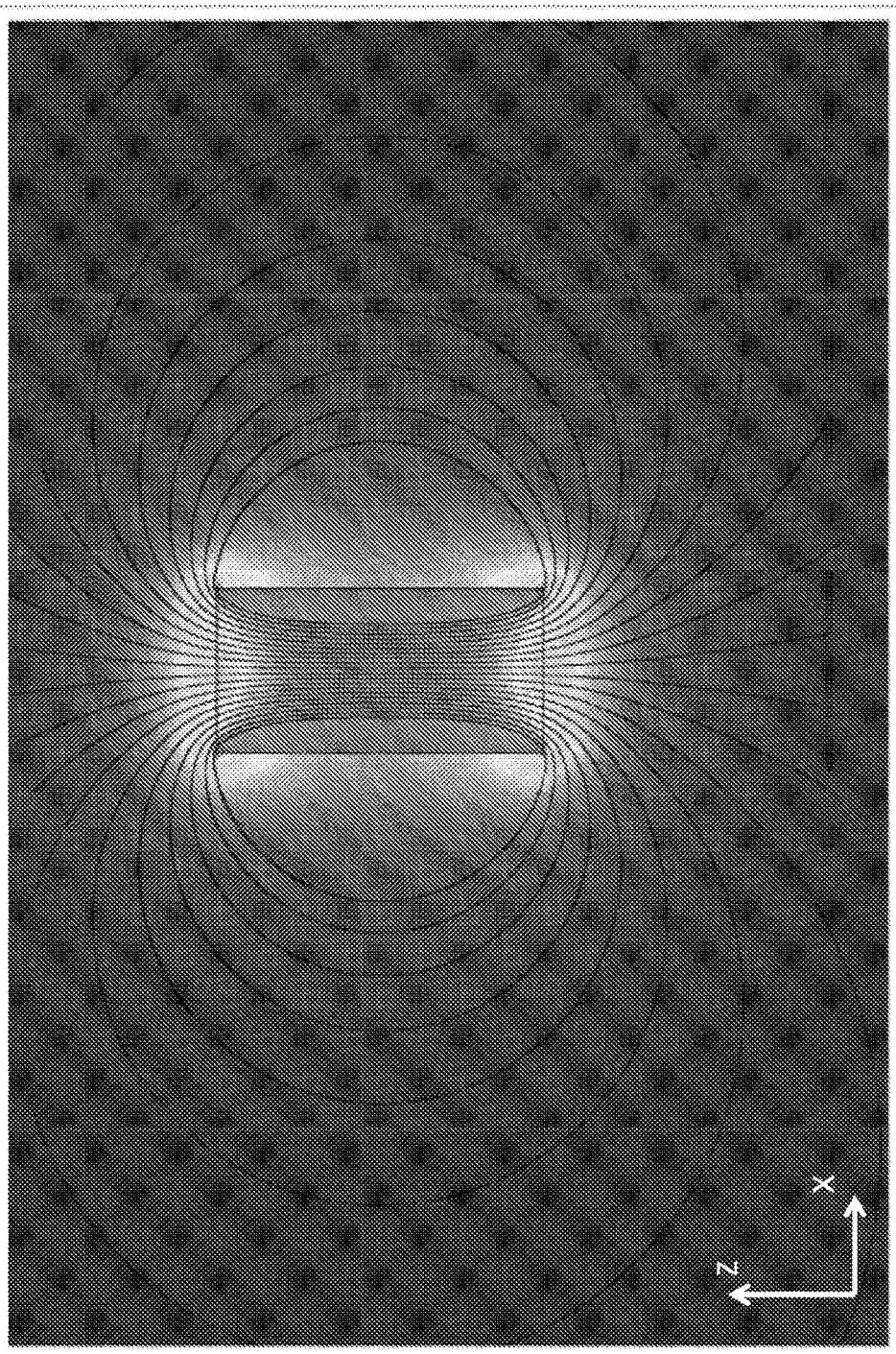
Figure 7B:
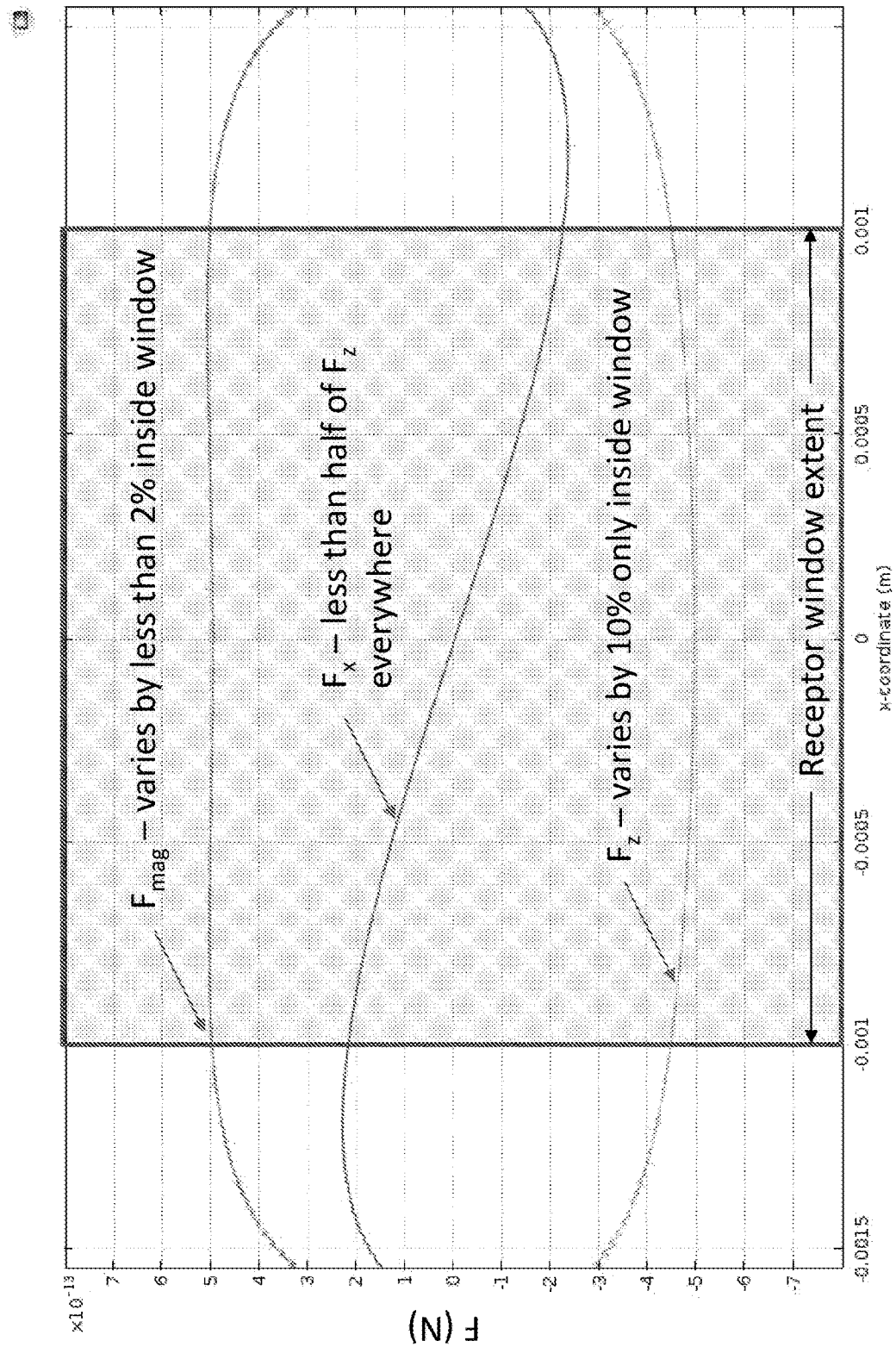
Figure 9A:
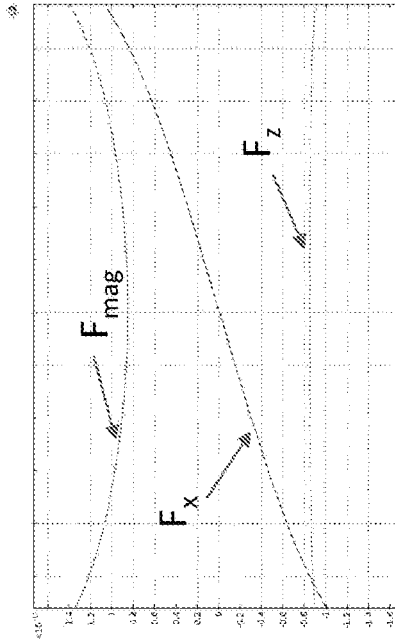
Figure 9B:
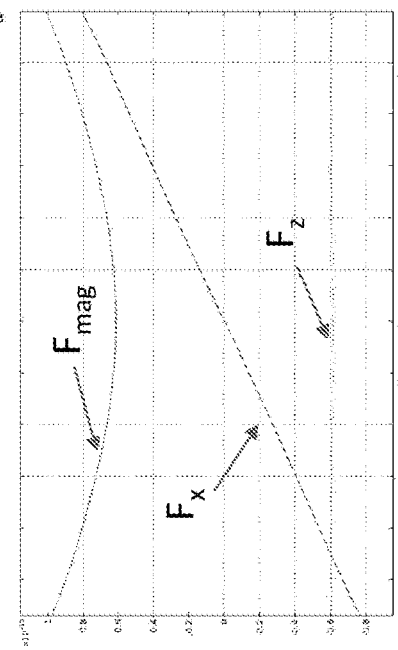
Figure 8A:
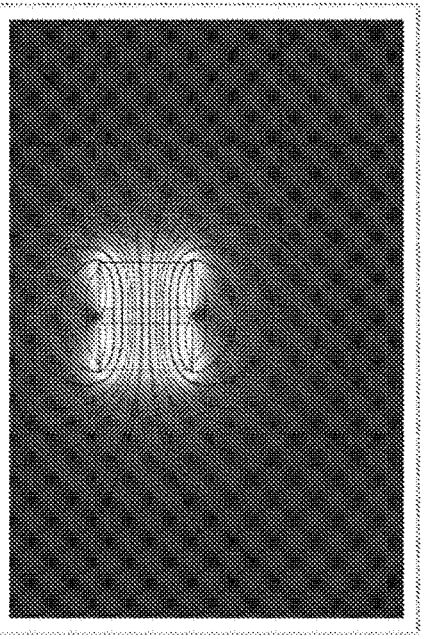
Figure 8B:
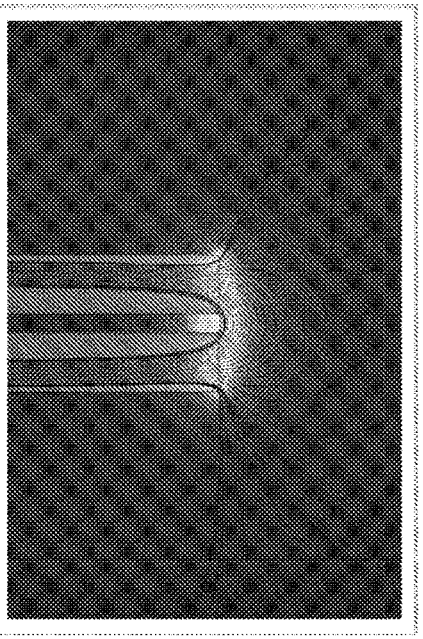
Figure 10A:
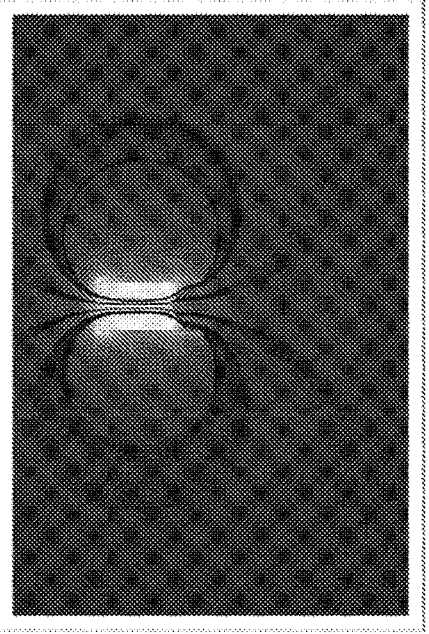
Figure 11A:
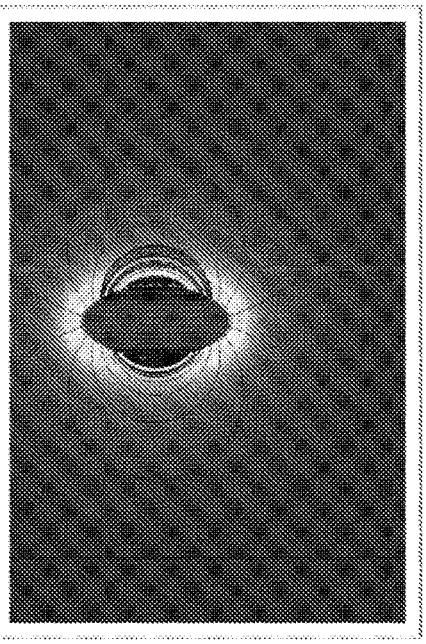
Figure 10B:
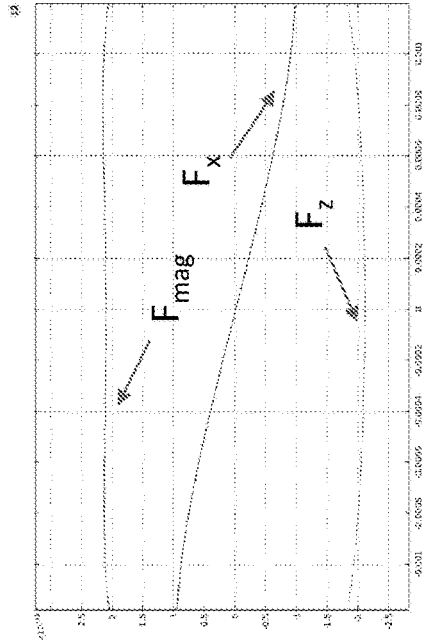
Figure 11B:
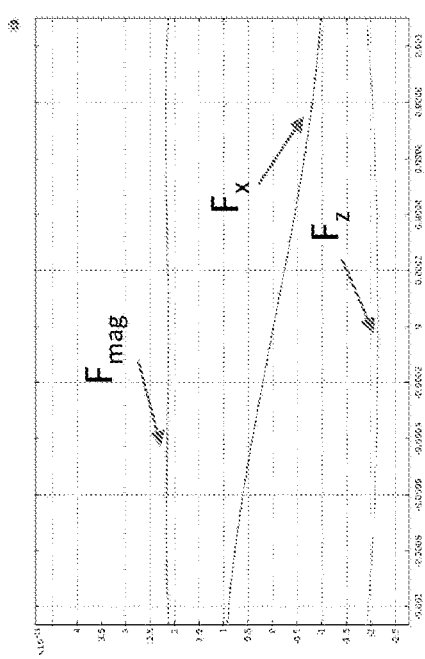

FIG. 5B shows an example schematic of a model used to simulate forces produced by a magnetic structure (a ring magnet in this example) configured for manipulating particles within a ferrofluid, according to some embodiments.

FIGS. 5C and 5D show example graphical illustrations of forces produced by a magnetic structure (a ring magnet in this example) configured for manipulating particles within a ferrofluid, according to some embodiments.

FIGS. 6A-11A show example magnetic flux density distributions of several magnetic structure configurations configured for manipulating particles within a ferrofluid, according to some embodiments.

FIGS. 5B-11B show example graphical illustrations of forces produced by magnetic structures (as depicted in the corresponding FIGS. 5A-11A) configured for manipulating particles within a ferrofluid, according to some embodiments.

Figure 12A:
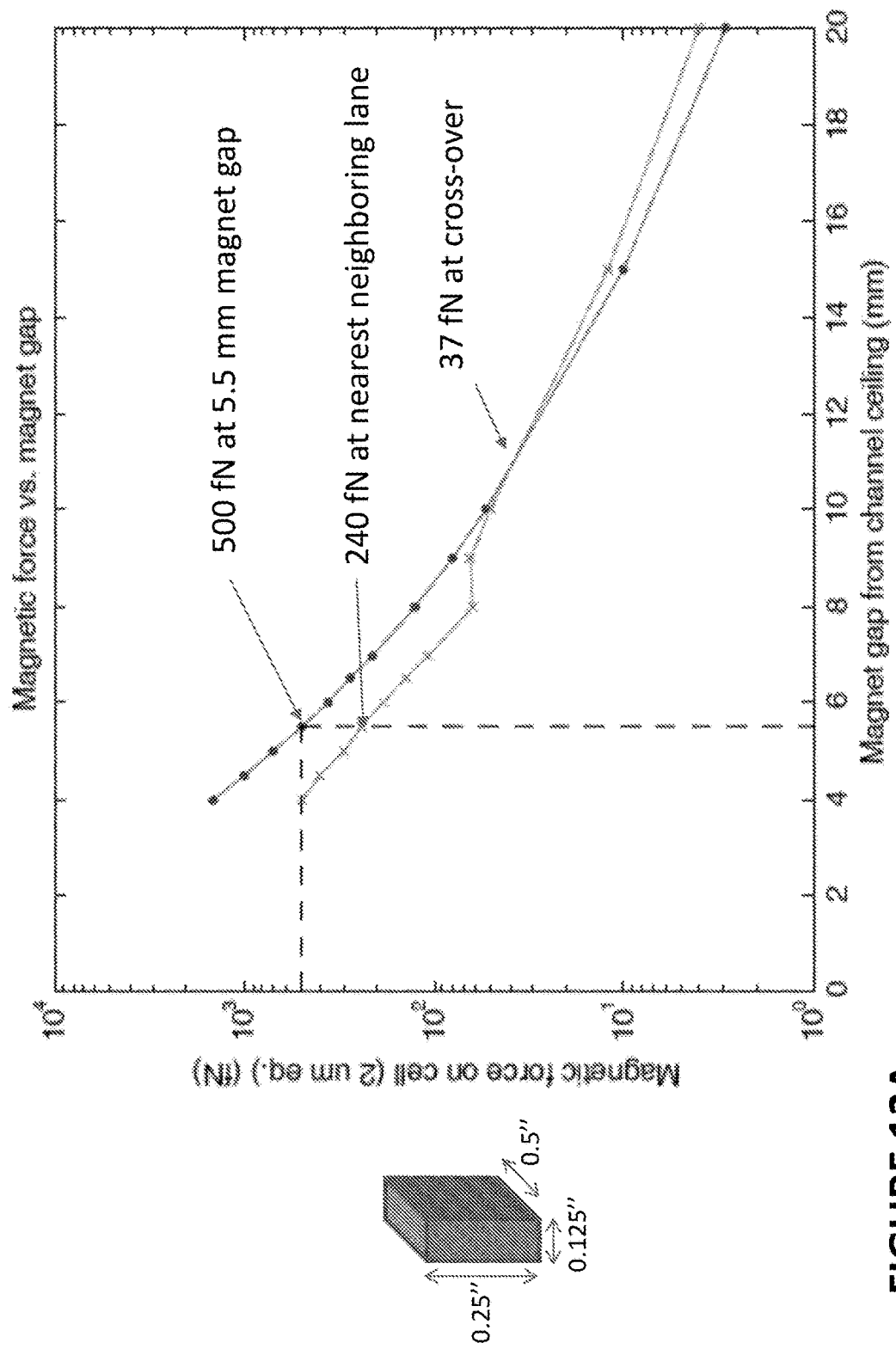
Figure 12B:
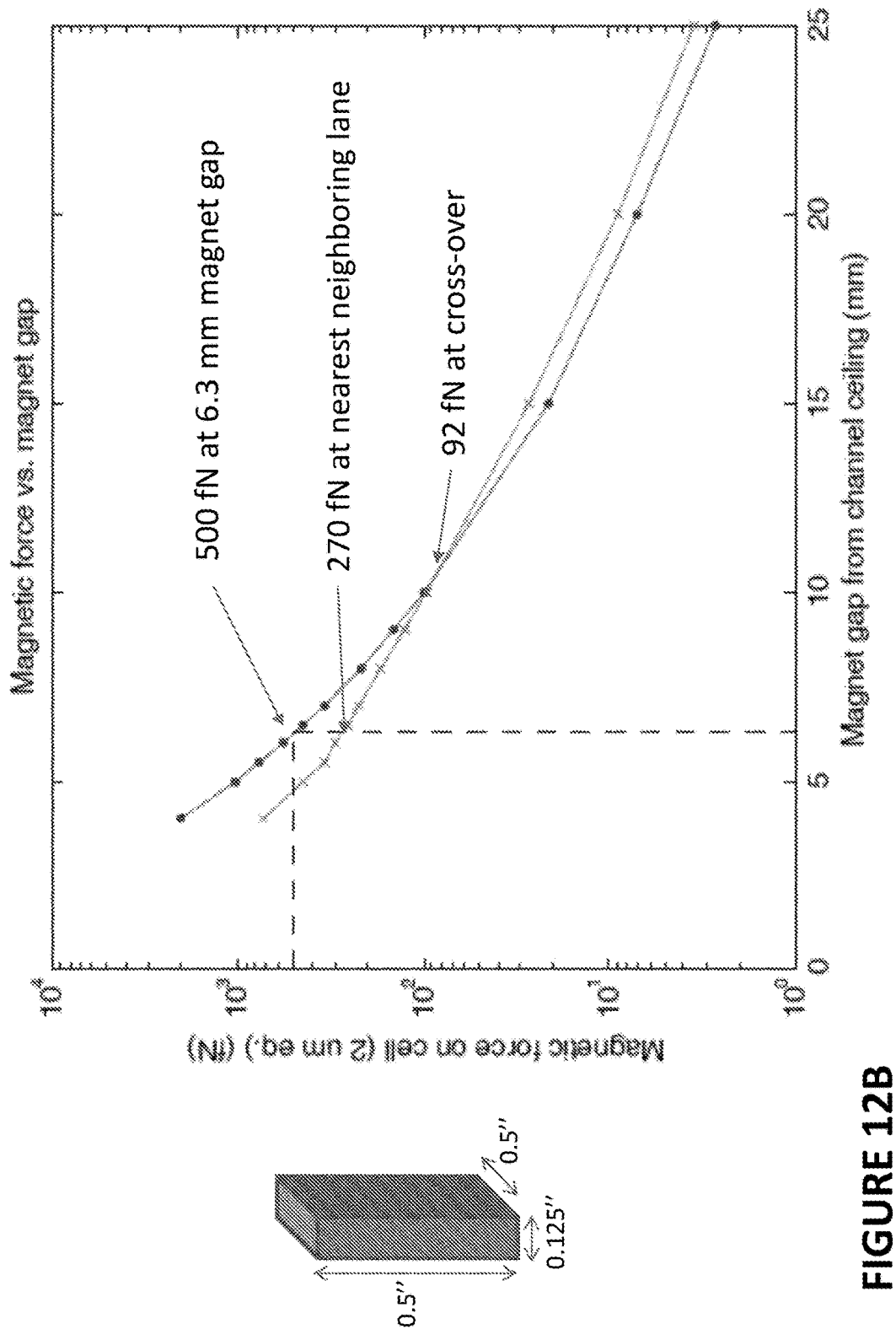

FIGS. 12A-B show example plots of magnetic forces versus magnetic gap (separation distance) of the magnet from receptor regions (located along channel ceilings), according to some embodiments.

DETAILED DESCRIPTION OF SOME OF THE EMBODIMENTS

In some embodiments, a ferrofluidic assay is presented which may include a fluidic channel having multiple electrodes arranged proximate thereto. A flow of a ferrofluid having target and background particles may be introduced into the channel (or provided in a channel or chamber and the like), and a capture region (also referred to herein as a "receptor region," "capture window" and "capture region") may be situated in a section of the channel (e.g., along an edge of the channel) to capture the target particles contained in the ferrofluid. Examples of target and/or background particles include typically whole, intact cells (such as bacteria, blood cells, other human or eukaryotic cells, etc.), non-magnetic microbeads (typically surface functionalized to bind to a specific target molecule and present it to the capture region in our assay). The term "target particle" or "target cell" refers to particles, beads or cells contained within a ferrofluid and are to be captured and/or extracted from the ferrofluid using the ferrofluidic assays. The term "background particle" or "background cell" refers to some or all of the other particles, beads or cells (i.e., other than the target particles, beads or cells) that are mixed with or to be found in the ferrofluid, and in particular those other particles, beads or cells that tend to be non-specifically captured in the receptor region. For example, when using the disclosed ferrofluidic assay to extract circulating tumor cells (CTCs) from a ferrofluid, the particles to be extracted, the CTCs, are to be considered as the target particles and other particles or cells are to be considered as background ones. In another example assay in the context of detecting *Salmonella* species bacteria within food samples, other native cells from the food item itself (such as chicken cells in a poultry assay) and other naturally occurring or contaminating bacteria species that are present in the food sample (such as *Escherichia coli* species) can constitute the background cells.

In some embodiments, the capture region may include functionalized receptor molecules that are configured to receive target particles or cells so as to form specifically captured or bound particles or cells. Examples of such receptor molecules include antibodies configured to capture the target particles, such as anti-Epithelial cell adhesion molecule (anti-EpCAM) antibodies configured to receive and/or capture CTCs, anti-*Salmonella* antibodies configured to receive and/or capture *Salmonella* species cells, etc. In some embodiments, the receptor particles may also receive or capture the background particles, forming non-specifically captured or bound particles or cells. This is especially prevalent and problematic for assays in which the background cells significantly outnumber the target cells; hence, a small percentage of the large number of background cells binding non-specifically to the capture region may end up crossing the detection threshold—causing a false positive assay result. In at least some of such cases, the target particles may be bound to the receptors with a force that is stronger than a weaker force adequate for capturing the non-specifically captured or bound particles, allowing for the use of a force intermediate between the stronger and weaker forces to dislodge and remove some or all of the background particles from the capture region. Such a force to dislodge and remove the background particles may be provided by the magnetic structures of the ferrofluidic assay.

In some embodiments, the magnetic structures may also generate a force that can be used to guide the flow of particles in the ferrofluid towards a particular section of the fluidic channel (e.g., towards the receptor region.)

In some embodiments, a variety of magnetic structures can be used to generate a magnetic field for manipulating the target and/or background particles in the ferrofluid, including causing particles within the fluid flow to deflect and be pushed towards a side (e.g., a ceiling) of the fluidic channel. Examples of the magnetic structures used to generate the magnetic field include one or more of electrodes (e.g., planar electrodes), electromagnets, permanent magnets, etc., and/or an array of any of the foregoing. Upon application of the magnetic field, particles may form a condensed stream along the side of the channel to which they are deflected (e.g., ceiling of channel), wherein the particles can roll thereon. When the particles reach the capture region, target particles can bind to receptor molecules. Background particles may also adhere to the capture region.

In some embodiments, additional magnetic structures can also be configured to generate an affinity thresholding magnetic field to further manipulate the target and/or background particles once the particles are captured in the capture region. For example, these magnetic structures such as an electromagnet, permanent magnet, and/or the like may be situated in the vicinity of the capture region (e.g., directly above the capture region) and may be used to detach and transport away some or all of the non-specifically captured particles. The magnitude, orientation and/or gradient of the additional magnetic field may be programmable, such that the forces of the field applied to the capture region can be changed/modified. For example, the magnetic field may be configured such that the nonspecifically bound background particles are sheared off the capture region while specifically bound target particles remain. Further, the magnetic field may be configured to shear off and remove the nonspecifically bound background particles (while retaining most or all of the specifically bound target particles, for example) far enough away from the particle detectors (e.g., optical scanners, scanning microscopes, etc.) such that the detectors would not detect the removed particles.

In some embodiments, a particle detector that is capable of distinguishing the target and background cells (e.g., based on a characteristic signal difference between the two types of cells) may be utilized to determine the number of background and/or target particles in various settings. Such a setup may be used for target cell enrichment, for instance, in the context of sample preparation for a subsequent processing step. For example, the detector may be used to determine an amount of the background particles which have been removed from the capture region. As an illustration, the detector may be configured to detect the number of non-specifically captured or background particles before and after the application of the magnetic field to determine the difference (i.e., determine number of un-removed background particles). In some embodiments, the magnitude, orientation and/or gradient of the additional magnetic field used to dislodge and remove the non-specifically bound particles may be based on the number of non-specifically bound particles captured in the receptor or capture region. For example, the change or modification to the magnitude, orientation and/or gradient of the additional magnetic field may depend on the number of non-specifically bound particles left unremoved after an application of a magnetic field to dislodge and remove them from the premise. For example, the additional magnetic field maybe be adjusted (e.g., increased) so as to reduce the number or proportion of non-specifically bound particles to a desired threshold amount (e.g., substantially zero). In some embodiments, the detector may also be used to determine the number of target particles captured by the capture region (e.g., determine that at least a minimum threshold number of target particles have been captured). Similarly, the amount of magnetic field applied by the magnetic structures so as to guide the flow of the target particles in the ferrofluid may depend and/or be adjusted based on the number or amount of target particles captured at the capture region. For example, if it is determined that a minimum threshold amount has not be captured, the magnitude, orientation and/or gradient of the magnetic field may be adjusted (e.g., magnitude increased, etc.) so as to increase the captured amount to at least the minimum threshold amount. Examples of such detectors include automated or otherwise scanning microscopes such as but not limited to optical scanners, sensitive mass balances, electroimpedance sensors, magnetic sensors, electrochemical sensors, and/or the like.

Figure 1:
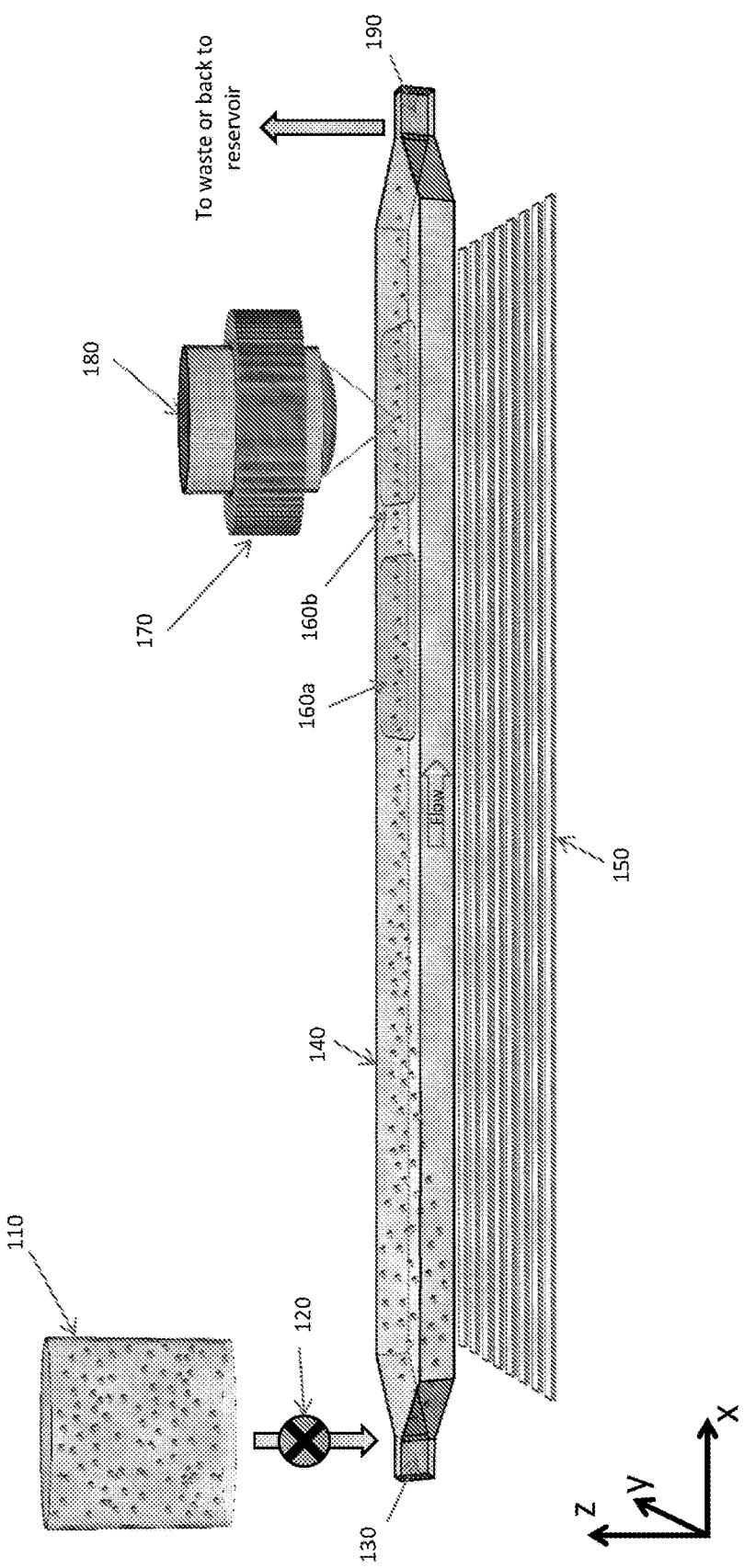
FIG. 1 is an example illustration depicting structures of a fluidic channel configured for extracting target particles within a ferrofluid, according to some embodiments.

FIG. 1 shows an exemplary configuration showing a flow of a mixture of target and background particles (e.g., cells, beads, etc.) and ferrofluid configured to receive them entering a channel 140 from a reservoir 110. In some embodiments, the fluid may be drawn into the channel using any one or more of gravity, a pump and/or pressure source 120 (for example). The flow enters the channel at an inlet 130, and as the flow enters the channel 140, the particles may be distributed relatively evenly throughout the flow and channel 140.

In some embodiments, magnetic structures 150 such as but not limited to planar electrodes, electromagnets, permanent magnetic arrays, etc., may be configured along one or more sides of the channel 140 for providing a magnetic force. The magnetic force can be used to push the target and background particles toward a side (e.g., a ceiling) of the channel 140. For example, in the configuration shown, the magnetic structures 150 may be situated along the bottom of the channel 140, and the magnetic force generated by the magnetic structures 150 may push the particles toward the ceiling of the channel 140. Thus, as the flow travels from the channel inlet 130 down the channel 140, the particles move towards the ceiling of the channel 140. In some embodiments, the magnetic structures 150 may extend along the entire length of the channel 140 (as shown in FIG. 1, for example) or only a portion thereof (e.g., up to the first or first few capture or receptor regions 160). One or more receptor regions 160a, 160b may be situated along the side (in this example, the ceiling) of the channel 140, and may be situated at a certain distance downstream of the inlet. In some embodiments, the placement of the receptor regions 160 and the strength of the magnetic field or force applied by the magnetic structures 150 may be interrelated. For example, the magnetic force may be configured such that most or all of the target particles are within the capturing reach of the capture molecules in the receptor regions 160. Such receptor regions 160 may extend along the entire side (i.e., ceiling) of the channel 140 or only a portion thereof.

In some embodiments, the magnetic structures 150 are configured such that the magnetic field generated by the magnetic structures 150 causes the target cells (e.g., cells, beads, etc.) to be pushed towards one side (e.g., from the bottom towards the capture regions at the ceiling) so that the target cells can roll and interact with the capture region strongly. The magnetic field may be strong enough to push the cells to the ceiling before they reach the capture region (or at least before they reach the end of the capture region). In some embodiments, the specific minimum strength of the field (for example, to facilitate the interaction of the target particles with the receptors in the capture region) can depend on the size of the cell/bead (e.g., larger cells can be pushed much faster), the flow speed (e.g., the faster the flow, the stronger the magnetic field can be so as to give the cells enough time to be pushed up before arriving at the capture regions).

In some embodiments, the maximum field strength can be determined by practicality concerns, such as but not limited to the desire to allow ferrofluid behavior to remain mostly linear (for example, minimize or avoid magnetic saturation of the ferrofluid, chain formation between its nanoparticles, etc.), the spacing between the magnet and the channel that is practically achievable, minimizing heating effects (e.g., in the case of electromagnets or planar electrodes), etc.

In some embodiments, each capture or receptor region 160 may have a plurality of receptors configured to specifically bind with one type of target particle. Each capture region may be configured to capture more than one type of target particle. Thus, multiple capture regions can be disposed within/along the channel, with each being configured (for example) to capture a different type of target particle (multiplex detection). Such multiple capture regions can also be configured to capture the same type of target particle. In some embodiments, the receptors may be antibodies configured to respond to specific types of target particles. As an example, antibodies such as anti-epithelial cell adhesion molecule (anti-EpCAM) antibodies configured to receive and/or capture CTCs within a ferrofluid.

In some embodiments, a second magnetic structure 170 may be located in the vicinity of the receptor regions 160 to produce an affinity thresholding magnetic field that can be used to affect the coupling of background particles to the receptor molecules. For example, the second magnetic structure 170 may include an electromagnet (AC or DC), permanent magnet, etc., situated above one or more of the receptor regions 160 and the generated magnetic field may be used to remove non-specifically bound particles from the receptor regions 160. A relatively uniform magnetic force at the center of the receptor region (corresponding to the field of view of the objective) may be obtained when the permanent magnet or the electromagnet 170 are wrapped toroidally around the magnet-scanner objective. This configuration for the magnetic structure may be used when addressing single, non-multiplex assays, i.e., fluidic channels with a single receptor region. In some embodiments, the application of the affinity thresholding magnetic field may be based on factors such as time elapsed since the start of ferrofluid flow, on whether the capturing phase of the ferrofluid flow is ongoing or complete, the amount of target and/or background particles captured in the capture region 160, and/or the like. For example, the affinity thresholding magnetic field may be applied after a set amount of time has elapsed (e.g., once the capture phase is complete, etc.). As another example, the affinity thresholding magnetic field may be applied periodically while the capture phase is ongoing (so as to allow periodic clearing of the capture region from background cells that would otherwise accumulate there, causing overcrowding and interfering with target cell capture). In some embodiments, the affinity thresholding field can be applied following (e.g., immediately) the capture phase and may also be applied without need for human interaction. And yet in some other embodiments, the application of the affinity thresholding magnetic field may depend on amount or concentration of specifically and/or non-specifically bound particles in the receptor regions 160 as measured by a particle detector 180.

The affinity thresholding magnetic field may be configured to remove background particles adhered to the capture region 160 without removing the target particles that are bound thereto. Alternatively, the affinity thresholding magnetic field may be tuned to remove a majority of the background particles that are adhered to the capture region 160 while removing only a small minority of the bound target particles. In some embodiments, the amount of magnetic field to be generated by the second magnetic structures 170 may depend on the amount of forces that may be needed to dislodge and remove the captured target and/or background particles. For example, in most embodiments, the bonding-strength of the force binding specifically-bound target particles to receptor molecules may be different than that binding non-specifically bound background particles. As such, the magnetic field generated may be configured or tuned so as to dislodge and remove from the receptor regions 160 determined amounts of target and/or background particles. For example, the magnetic field may be tuned such that the magnetic force applied in the receptor regions 160 dislodges and removes about all or substantially all of background particles but about none or almost none of the target particles (e.g., the magnetic force may be tuned to be in between a larger force that would dislodge a specifically-bound target particle and a smaller force that would dislodge a non-specifically-bound background particle, thereby removing at least most background particles but no or very few target particles).

In some embodiments, the affinity thresholding magnetic field to be generated by the second magnetic structure 170 so as to produce the magnetic force to dislodge and remove the background particles may also depend on the properties of the ferrofluid (e.g., magnetic properties such as magnetic susceptibility, fluidic properties such as viscosity (that in part determines how fast dislodged particles will move away from the capture region) and ionic strength (that determines in part the affinity between the capture receptor and the ligand on the cell or particle surface), etc.), the separation distance of the second magnetic structure 170 from the receptor or capture regions 160, the size (mass, volume, etc.) and density of the target and/or background particles, and/or the like. For example, the magnetic properties of the ferrofluid may include its magnetic susceptibility, to which the magnetic field may couple to generate the force. The magnitude and gradient of the affinity thresholding field, together with the magnetic susceptibility of the ferrofluid, can determine the magnitude of the push force on the cells and/or microbeads in the ferrofluid. In some embodiments, an electromagnet may be used to generate the affinity thresholding magnetic field and the magnitude, gradient, orientation, etc., of the affinity thresholding magnetic field may be tuned by controlling the amplitude of the excitation current. Further, the separation distance of the magnetic structure 170 may be varied so as to tune the magnetic force to be applied in the capture region 160. For example, a permanent magnet may be used to generate the affinity thresholding magnetic field and the affinity thresholding magnetic field can be tuned by changing the height of the permanent magnet with respect to the capture region 160. In some embodiments, such functionality can be configured to tune the force in real time. In other embodiments, the dimensions of the permanent magnet can be changed.

In some embodiments, the fluidic properties of the ferrofluid may include viscosity, density, etc. Such properties may in particular affect the removal of the non-specifically bound background particles once they are dislodged from the receptors. For example, the magnetic force may exert a force to remove the dislodged particles away from the receptor or capture regions 160 so that the particle detectors or scanners 180 would not detect them. The amount of force to be exerted may then depend on the volume of the removed particles, the density and viscosity of the ferrofluid, and/or the like.

In some embodiments, particles that do not bind to the receptor regions 160 and any particles that shear off of the receptor region 160 when the affinity thresholding magnetic field is applied could continue flowing along the channel towards a channel outlet 190, which can be sent to a waste area. In some embodiments, the remaining flow may be sent back or recycled to the reservoir 110 such that remaining target particles can be removed from the flow.

In some embodiments, a plurality of channels (not shown) may be provided so that the ferrofluid flowing out of one channel enters another channel. For example, a remaining flow from one channel may go through a second channel with a similar configuration in order to remove additional target particles. In some embodiments, the second channel may be configured to capture a different target particle that is contained within the ferrofluid. Thus, a particle that was a background particle in a first channel configuration can be a target particle in a subsequent channel configuration. This can be achieved by using different capture molecules in the receptor regions in the second/other channels and/or by altering the first magnetic field and the affinity thresholding magnetic field in such other channels.

In some embodiments, a detector 180 may be used to determine whether background particles, or at least some of the background particles, have been removed from the capture region 160 and/or whether target particles (and/or an amount thereof) have been captured. For example, the detector 180 may determine that the amount of background particles on the capture region is over a threshold percentage or threshold number of background particles. The percentage may refer to the proportion of background particles to target particles or total number of particles in the capture or receptor regions 160. As noted, the detector 180 (or second detector) may also be used to determine that at least some target particles, or at least a certain amount (number or percentage) of target particles, have been captured by the capture region 160. Similarly, the percentage may refer to the proportion of target particles captured to total captured particle count or initial target particle amount (e.g., compared to known or expected amount of target particles in the reservoir 110). In some embodiments, the detector 180 may be an optical scanner (e.g., an automated scanning microscope), a sensitive mass balance (e.g., a quartz crystal mass-balance (QCM)), an electrochemical sensor (e.g., may be an electrochemical sensor configured to respond to the presence of live cells metabolizing over a surface of the capture region), and/or the like. For example, a ferrofluid may be configured to receive and contain CTCs (example target particles) and white and red blood cells (example background particles), and a detector such as a scanning microscope may distinguish between the target and background particles based on size, morphology and fluorescence signal from a specific label (if used).

In some embodiments, the capture regions 160 connected to the channel 140 may be removable. For example, once a capture region 160 is determined to have at least a threshold (number or percentage) of target particles and/or determined to have below a certain threshold (number or percentage) of background particles, the capture region 160 may be removed from the channel (e.g., for further processing, such as PCR or genomic sequencing on the captured cells). In some embodiments, the removed capture region may be replaced with a new capture window. In some embodiments, the capture regions 160 may be irremovable, i.e., monolithically integral with the fluidic channel 140.

In some embodiments, if a capture region 160 is determined to lack at least a threshold amount (number, percentage, etc.) of target particles, the flow may be reinitiated/continued and another first magnetic field may be applied, followed by another second magnetic field. Thereafter, the detector may perform another test, and this process may continue until the detector senses that a sufficient amount (number or percentage) of target particles have been captured by the capture window. In these contexts, the percentage may refer to the proportion of target particles captured to total captured particle count or initial target particle amount (e.g., compared to known or expected amount of target particles in the reservoir 110).

Figure 2:
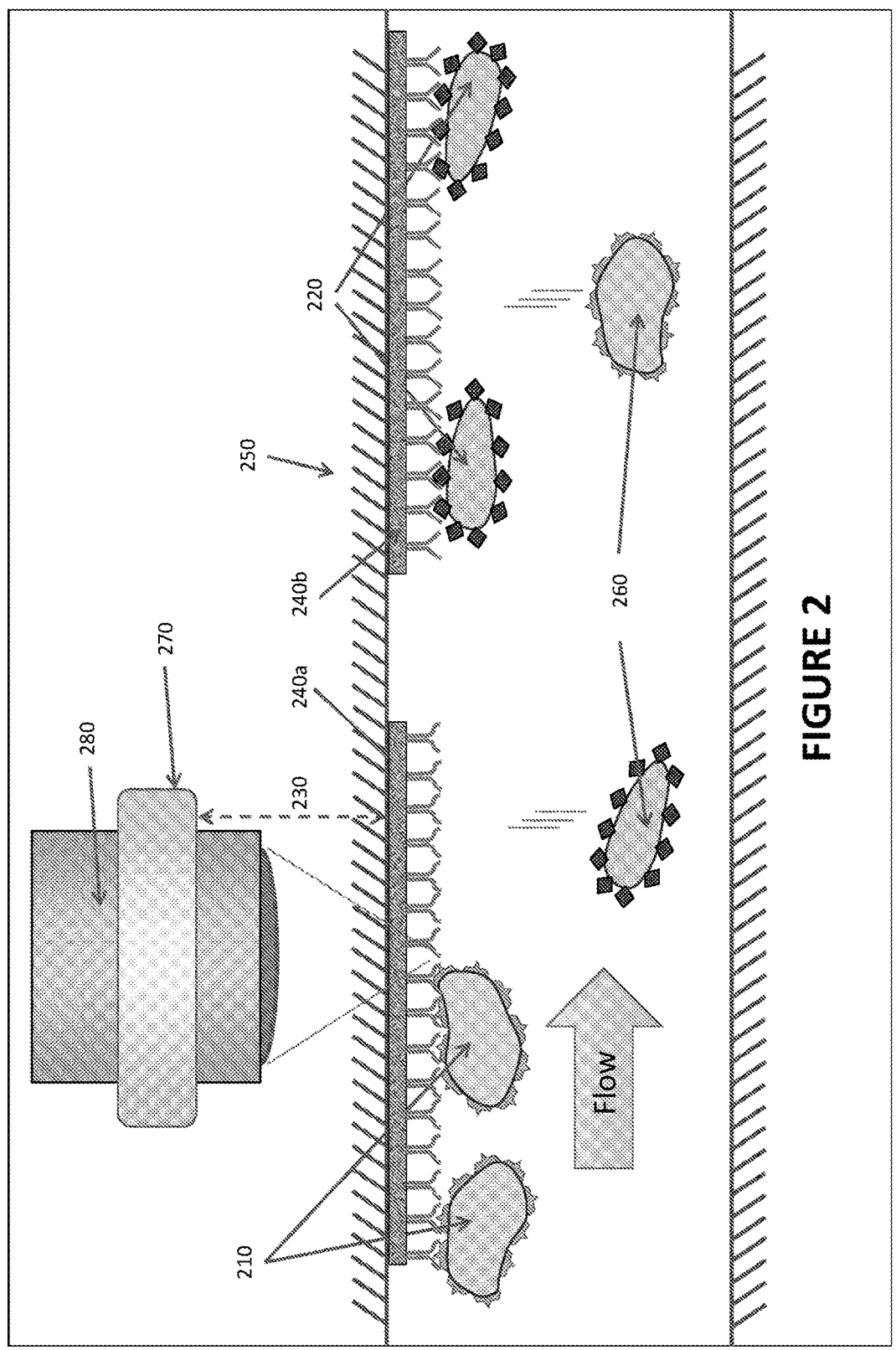
FIG. 2 is an example illustration depicting structures of a fluidic channel and associated structures configured for manipulating and monitoring particles within a ferrofluid, including capture regions, magnets, and optical scanner, according to some embodiments.

FIG. 2 illustrates an example embodiment of the functioning of a fluidic channel 250 and associated structures configured for manipulating and monitoring particles contained within, or added to, a ferrofluid, including capture regions 240, magnets 270, and detectors 280 such as optical scanners (for example). As a ferrofluid flow moves through the channel 250, a first magnetic field generated by first magnetic structures (not shown) such as planar excitation electrodes, electromagnet, or permanent magnet located beneath the channel 250 push the particles away from the side of the channel 250 that is proximate to the first magnetic structures (e.g., toward the top of the channel 250 as shown in the FIG. 2). The channel 250 may include one or more capture or receptor regions 240a, 240b, where a region may contain one or more types of capture molecules for trapping corresponding target particles. For example, capture region 240a may be configured for capturing one type of target particles 210 and capture region 240b may be configured to capture a different type of target particles 220. As such, capture regions 240a and 240b may include capture molecules or antibodies that may be configured to capture the respective target particles 210, 220, and the respective target particles 210, 220 may specifically bind to the capture region 240, 240b. In some embodiments, a single capture region may be configured to capture more than one type of target particles, and as such may contain more than one type of capture molecules. Some background particles 260 may also adhere to the capture regions 210, 220 (i.e., nonspecifically binding). Particles may be considered as background particles 260 to a particular capture region when those particles are the ones not configured to be captured by that region. For example, for capture region 240a, target particles 220 of the capture region 240b may be considered as background particles 260, and vice versa. Each capture region may capture a different amount of background particles.

In some embodiments, this affinity thresholding approach may be used to enrich the population of a particular type of particles for further use. For example, a ferrofluid having a certain cell population may be purified so as to remove most or all other particles that are not the cell population. The enriched or purified cell population can then be further processed by other experimental techniques such as polymerase chain reaction, genomic sequencing, flow cytometry, etc. In purifying the ferrofluid to enrich the particular cell population, for example, the fluidic channel may be equipped with capture regions comprising receptors configured for capturing the particular cells. For example, to purify a population of CTCs in a ferrofluid, a fluidic channel may be provided with receptor regions having anti-epithelial cell adhesion molecule (anti-EpCAM) antibodies configured to receive and/or capture CTCs. Similarly, to capture and purify *Salmonella* species bacteria in a food sample (such as poultry, etc.) mixed with ferrofluid, anti-*Salmonella* antibodies may be configured to receive and/or capture *Salmonella* species cells. Once the ferrofluid flows through the channel and some or all of the cells (target particles as well as other (background) cells) are captured by the receptors, the affinity thresholding approach disclosed herein may be employed to discard most or all of the background particles, leaving behind a purified or enriched cell population, which can then be used for further purposes (e.g., further processing).

The type of interaction force that binds one type of particle to a corresponding receptor particle in a receptor region may be different than the type of interaction for a different particle-receptor pair. Accordingly, the specific interaction force for each particle may be different as the force may also depend on a number of binding events for each particle, the nature of the binding, and whether the binding is specific or nonspecific. This means that for each particle bound to a corresponding receptor (e.g., antibody or receptor molecule) in the capture region, there may be a threshold force above which the captured particle may shear off of the capture region and return to the ferrofluid flow in the channel (or simply move deeper into the ferrofluid and away from the capture surface, thereby not getting registered by the sensor). In most cases, the force that binds the particles that are specifically bound to the capture region (e.g., target particles) may be larger than the force for non-specifically bound ones (e.g., background particles), and as such magnets 270 may generate a magnetic field to produce a range of magnetic forces that rip off and remove background nonspecifically bound particles 260 from a capture region 240 without affecting at least a substantial amount of specifically bound target particles 210. One way to vary the strength of the magnetic field (and consequently the magnetic force, for example) is by varying the separation distance 230 of the magnet from the capture regions 240. A range of magnetic field strengths configured for optimizing an amount of specifically bound target particles (amount as measured in terms of a ratio of the remaining specifically bound particles to the remaining non-specifically bound particles, for example) can be determined for each particle-receptor pair, and this range may be attained by varying the separation distance 230 of the magnet 270 (for a permanent magnet, for example). For an electromagnet, as noted above, the range of magnetic field strengths may be controlled and tuned by varying the amplitude of the excitation current of the electromagnet. The tuning of the magnetic strength by optimizing the separation distance 230, tuning the excitation current and/or other means allows for enhancing the sensitivity and specificity of the assay, facilitating the use of the disclosed tunable affinity thresholder for any ferrofluid-based capture assay. FIGS. 3A-B schematically show an embodiment where a magnet 320 with a variable height or separation distance 330 from receptor or capture regions 340 moves up and down so as to vary the strength of the magnetic force applied at the receptor regions 340. For example, once a ferrofluid flows through a fluidic channel and target and/or background particles are captured at capture regions 340, the magnet 320 may be moved closer to the capture regions 340 as shown in FIG. 3B so as to magnetically force background particles bound to receptors or antibodies to dislodge and move away from the receptor regions 340. The magnet 320 may be lowered to an optimal height for an optimal target particle concentration, for example. A detector or a scanner 310 then may be used to detect (e.g., take images, etc.) and determine the amount of target and/or background particles still bound to the capture regions 340. In some embodiments, a series of images may be taken as the height 330 is varied to determine the optimal height for the magnet 320 to produce the optimal magnetic force. In some embodiments, for example as shown in FIG. 3C, the steps of defocusing (i.e., dislodging and removing) of background particles by a variable height magnet 320 followed by scanning and detecting still-bound particles (target and/or background) by a detector/scanner 310 may be employed over a plurality of receptor or capture regions 340 in one fluidic channel device, allowing for expedited and efficient ferrofluid-based capture assay of target particles. For example, the plurality of receptors 340 may be arranged as a series of wells configured to contain ferrofluids (including target particles such as cells and/or microbeads) and spaced apart on a microwell plate 330. The wells may be covered or opened individually, allowing one to select some of the wells to stay open (and as such be part of the operation) and others closed during the operation of the fluidic channel. The microwell plate 330 may also be configured to be removably coupled to the fluidic channel, allowing for the use of disposable receptors 340 in executing the affinity-thresholding approach for capturing and extracting target particles disclosed herein.

In some embodiments, the spacing between the receptors 340 may be chosen so as to avoid the "cross-talking" of magnetic field lines to neighboring receptor regions when a specific receptor region is being interrogated by the affinity thresholder (for example, when the magnet is addressing the specific receptor region). For example, in a multiplex assay including a plurality of receptors (e.g., an array or matrix of capture or receptor regions), the effect of magnetic fields from a magnet addressing a receptor region may be substantial on neighboring receptor regions (e.g., as far away as from a diameter to twice the diameter of the toroidal magnet). As such, the receptor regions may be spaced apart from each other by up to about a diameter, about 1.25 times the diameter, about 1.5 times the diameter, about 1.75 times the diameter, about twice the diameter, etc., of the magnet being used in the assay process. In some embodiments, the magnet may be made as small as possible while providing adequate amount of magnetic force to remove captured background particles. Further, other configurations such as rectangular magnets with small linear dimensions or cylindrical magnets with reduced diameters (compared to toroidal magnets, for example) may be used to minimize or avoid "cross-talking" of magnetic forces between neighboring receptor regions. For example, a rectangular magnet with linear dimensions (e.g., width) about same as or less than the separation distance between neighboring receptor regions may be used to minimize or avoid "cross-talking" of magnetic forces. For cylindrical or other circular configurations, the diameter of these configurations may be made to be about equal to or less than the receptor region separation distance so as to minimize or avoid "cross-talking" of magnetic forces.

As discussed above, the type of interaction force that binds one type of particle to a corresponding receptor particle (e.g., antibodies, surface biomarkers, receptor molecules, etc.) in a receptor region may depend on a number of factors, including the number and nature of specific binding events for each particle, whether the binding is specific or nonspecific, and/or the like. In some embodiments, one may utilize the above affinity-thresholding approach for capturing and extracting target particles to determine the binding affinity strength of the captured particles to the receptor particles. For example, the magnetic force strength may be varied until the interaction force that binds a particle to its corresponding receptor particle is broken under the force of the magnetic field. Such variation may be achieved by a number of techniques including changing the separation distance of the magnet from the capture region, tuning the excitation current of an electromagnet, etc. When the magnetic force exceeds the binding affinity strength of the target-receptor particle pair, i.e., when the magnetic force exceeds the interaction force between the constituents of the pair, the pair bond may break, indicating that the applied magnetic force is at least substantially equal to the binding affinity strength. As such, one may determine binding affinities using an affinity thresholding approach as described herein.

FIG. 4A-J shows several example configurations for arranging magnetic structures such as permanent magnets and electromagnets so as to provide a substantially uniform magnetic force on receptor regions (e.g., antibody windows) that is at least strong enough to break the bond between a receptor and a captured background particle. In some embodiments, the magnetic structures may include a single magnet with either the north or the south pole located proximate to the receptor regions of the fluidic channel (e.g., FIGS. 4D, 4E, and 4H), or in some cases, the magnets may be positioned in a substantially parallel manner to the channel so that both the north and south pole of the magnets are proximate to the receptor regions (e.g., FIGS. 4F, 4G, and 4I). In some embodiments, the strength of the magnetic force from these single magnets may not depend on their orientation, i.e., it may not depend on the polarity of the magnet facing the channel. When there is more than one magnet, however, the relative polarity between neighboring magnets may affect the strength of magnetic force felt at the receptor regions. As such, the relative orientation of the magnets with each other may be used as a control parameter to vary the magnetic field that would be applied to background particles captures at the receptor regions.

FIGS. 5-12 show example several simulation results for magnetic field profiles and magnetic force components applied in receptor regions proximate to the magnets producing the magnetic profiles. FIG. 5A shows the magnetic field profiles of an example toroidal magnet with a diameter smaller than the dimensions of a receptor window (FIG. 5B), all depicted in 2D cylindrical coordinates across the rz plane. Both the radial dimensions of the magnet (i.e., its inner and outer radii), as well as the resulting magnetic forces exerted on a 2 micron diameter micro bead or cell suspended in a common ferrofluid, are depicted in FIGS. 5C and 5D. FIG. 5C illustrates that the magnetic force along the z-direction (i.e., the longitudinal force from the magnet to the receptor regions) in the vicinity of the receptor region is basically uniform (at 50 fN (femtoNewtons)) within half the inner radius around the center axis of the toroidal magnet (labeled "magnet" in FIGS. 5C and 5D). For example, in the particular embodiment of FIG. 5C, $F_z$ represents the force applied by the magnet at the receptor region or window ("simulated receptor window") in the perpendicular direction at a distance of approximately 5 mm, and the force is shown to range from about 50 fN under the center axis of the magnet to about 500 fN under the magnet ring. In the preferred embodiment, the receptor region would be located within half the inner radius under the center axis of the magnet, and the magnet moving in the z-direction would provide the desired tunability of the magnetic force (larger forces with smaller gaps). As such, a background particle captured by a receptor in the receptor region would experience a uniform magnetic force in the perpendicular direction, i.e., a force that attempts to break the affinity bond between the receptor and the captured background particle and drive the particle away from the receptor region (so as to avoid detection of the background particle by a detector or a scanner, for example). Alternatively, the magnet may be scanned along the radial direction, and the maximum force at a given gap (500 fN in this example's gap) corresponds to the effective affinity thresholding force.

As discussed above, an application of a relatively large force (e.g., about 500 fN, about 450 fN, about 400 fN, etc.) may rip or dislodge a captured background particle from a receptor and remove it from the receptor region to avoid a scanner or detector from detecting the background particle. However, there may be other forces that act on the particle, such as the buoyancy provided by the ferrofluid surrounding the background particle. Since the buoyancy force may push back the background particle towards the receptor regions, the magnetic force may be configured to remove the background particle for at least enough amount of time so as to allow the scanner or detector to scan the receptor region before the return of the background particle. Net buoyancy of a particle or a cell is given by $F_{b,net} = gV_{cell}(\rho_f - \rho_{cell})$ where g is acceleration due to gravity, $V_{cell}$ is the volume of the background particle or cell, $\rho_{cell}$ is the density of the cell and $\rho_f$ is the density of the ferrofluid. Using typical values for the volume and densities corresponding to the ones used in generating FIGS. 5A-5D, the buoyancy force may be about 8 fN, in contrast to the about 500 fN of the magnetic force applied to remove the background particle or cell. To determine the relationship between the lengths of time it may take for the magnetic force to remove the background particle away and for the buoyancy force to return it back, in some embodiments, one may use Stokes' drag equation to calculate the drift velocities of the background particle in the two situations: $v_{drift} = F/(6\pi\eta r)$, where $V_{drift}$ is the drift velocity, $\eta$ is the ferrofluid viscosity, r is the so-called Stoke's radius and F is the total force applied on the background particle (e.g., 500 fN-8 fN when the particle is being removed and only 8 fN when the particle is being buoyed back). Again, using the values of the particular embodiments of FIGS. 5A-D and assuming a 2 micron particle or cell, it may take about 60 times as much time for the background particle to be buoyed back up as it would take for the magnetic force to remove the particle. In some embodiments, the magnet and the ferrofluid may be configured so as to allow a determined amount of time before a background particle buoys back to a receptor region after removal by a magnetic force (e.g., at least as much or more time than would be needed to scan a receptor region). Such a determined amount of time may be such that, for example, it may take about 5, about 10 times, about 20 times, about 40 times, about 60 times, about 80 times, about 100 times, etc., as much time for the background particle to be buoyed back up as it would take for the magnetic force to remove the particle. Since both the magnetic force and the buoyancy force are proportional to or scale with the volume of the background particle, the proportion of the above-noted times is substantially independent of the volume of the particles. For example, for the same magnetic field, smaller particles may be removed slowly as compared to larger particles, but conversely, the buoyancy force would return them back to the receptor regions similarly (and proportionally) slowly.

FIGS. 6A-11B show simulation results of magnetic field profiles and magnetic force components applied in receptor regions for additional magnet configurations including horizontal rectangular magnet (FIGS. 6A-B), vertical rectangular magnet (FIGS. 7A-B), and rectangular magnets oriented in between vertical and horizontal and symmetric about a receptor window (FIGS. 8A-11B). In at least most of these cases, for example as shown in FIGS. 8B, 9B, 10B and 11B, the longitudinal magnetic force acting to remove the background particles ($F_z$) can be substantially uniform and may vary by at most a small amount in the receptor region or window. This may be the case even when the nominal magnetic force ($F_{mag}$) is non-uniform, as shown, for example, in FIG. 6B. It is also to be noted that in almost all magnet configurations, the magnitude of $F_z$ exceeds that of $F_x$, the transverse component (i.e., at least substantially parallel to the width of the receptor regions or windows) of the magnetic force, indicating that the longitudinal force ($F_z$) on the background particles as they are being pushed away and ripped off from the capture region is more substantial than the transverse force ($F_x$).

FIGS. 12A-B show example plots of magnetic forces versus magnetic gap (separation distance) of the magnet from receptor regions (located along channel ceilings), according to some embodiments. As discussed above, optimal magnet gap or separation distance (between magnets and reception or capture regions) may be determined by varying the separation distance and detecting the amount of captured background particles that are left over (or removed from) the receptor regions. In such embodiments, it is desirable to have the change of the magnetic force as the separation distance is changing to be gradual and/or small. In other words, it is desirable for the gradient of the nominal magnetic force to be small, finite and constant, i.e., for $$-\frac{\partial F_{mag}}{\partial h} < K,$$

where $F_{mag}$ is the magnetic force, h is the separation distance and K is an upper bound for the magnitude of the gradient (in most embodiments, positive, constant and small value). When this condition is fulfilled, the changes in the magnetic force applied to the captured background particles can become gradual and small, i.e., the use of the affinity threshold approach as disclosed herein can become more controllable and repeatable. In some embodiments, for example for parameters used in the simulations of FIGS. 4A-11B, K can attain a value of about 0.3 nN/m (FIGS. 12-B). In some embodiments, K can have values ranging from about 0.05 to about 1 nN/m, about 0.01 to about 0.5 nN/m, about 0.2 to about 0.4 nN/m, etc.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings disclosed herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to target particle separation, focusing/concentration. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may include negative limitation to specifically exclude one or more elements/features resulting in embodiments which are patentably distinct from the prior art which include such features/elements.

What is claimed is:

1. A system, comprising:
a fluidic channel or chamber configured to include a ferrofluid having a plurality of target particles and background particles;
a capture region located along a first side of the fluidic channel functionalized with a plurality of receptor particles configured to capture at least a portion of the plurality of target particles,
a first magnetic field generator arranged proximate to the fluidic channel, wherein the first magnetic field generator:
includes electrodes running along at least a section of a second side of the fluidic channel, the second side being opposite to the first side, and
is configured to generate a first magnetic field configured to direct the plurality of target particles towards the capture region;
and
a second magnetic field generator arranged proximate to the capture region, the second magnetic field generator configured to generate an affinity thresholding magnetic field configured to remove background particles from the capture region.

2. The system of claim 1, wherein the affinity thresholding magnetic field is configured to remove background particles which are captured by at least a portion of the plurality of receptor particles.

3. The system of claim 1, further comprising a detector configured to detect the at least a portion of the plurality of target particles captured by the plurality of receptor particles.

4. The system of claim 1, wherein the plurality of target particles comprise cells, including one or more of bacteria, blood cells, and eukaryotic cells.

5. The system of claim 1, wherein the plurality of target particles include non-magnetic microbeads.

6. The system of claim 1, wherein the capture region includes a plurality of capture regions, each capture region functionalized with a plurality of receptor particles configured to capture same type of target particles.

7. The system of claim 1, wherein the capture region includes a plurality of capture regions, a first capture region functionalized with a plurality of receptor particles configured to capture a different type of target particle than a second capture region of the plurality of capture regions.

8. The system of claim 1, wherein the second magnetic field generator includes a permanent magnet and/or an electromagnet.

9. The system of claim 1, wherein the second magnetic field generator includes an electromagnet, and a strength of the affinity thresholding magnetic field is controlled by varying an amplitude of an excitation current of the electromagnet.

10. The system of claim 1, wherein the second magnetic field generator includes a permanent magnet, and a strength of the affinity thresholding magnetic field is controlled by varying a separation distance between the second magnetic field generator and the fluidic channel is adjustable.

11. The system of claim 1, wherein a magnitude of a gradient of an affinity thresholding force corresponding to the affinity thresholding magnetic field along a separation distance separating the second magnetic field generator from the fluidic channel is less than a threshold gradient value.

12. The system of claim 1, wherein a force applied by the affinity thresholding magnetic field on the at least a portion of the plurality of target particles captured by the plurality of receptor particles is less than an affinity bond strength of a target particle to a receptor particle.

13. The system of claim 3, wherein the detector includes an automated scanning microscope.

14. The system of claim 3, wherein the detector includes a sensitive mass balance.

15. The system of claim 3, wherein the detector includes an electrochemical sensor.

16. The system of claim 3, wherein the detector includes an electroimpedance sensor.

17. The system of claim 3, wherein the detector includes a magnetic sensor.

18. The system of claim 1, wherein the fluidic channel is configured to receive a flow of the ferrofluid flow.

19. The system of claim 1, wherein the affinity thresholding magnetic field is further configured such that after the removal of the background particles from the capture region, a force applied by the affinity thresholding magnetic field on captured target particles breaks an affinity bond strength between the captured target particles and corresponding receptor particles to release the captured target particles.

20. The system of claim 19, further comprising an outlet configured to collect the released target particles for storing and/or further processing.

21. A system comprising:
a fluidic channel or chamber configured to include a ferrofluid having a plurality of target particles and background particles;
a capture region located along a first side of the fluidic channel functionalized with a plurality of receptor particles configured to capture at least a portion of the plurality of target particles,
a first magnetic field generator arranged proximate to the fluidic channel, the first magnetic field generator configured to generate a first magnetic field configured to direct the plurality of target particles towards the capture region;
and
a second magnetic field generator arranged proximate to the capture region, the second magnetic field generator configured to generate an affinity thresholding magnetic field configured to remove background particles from the capture region,
wherein:
the capture region includes at least a first capture region and a neighboring second capture region,
and
a spacing between the first capture region and the second capture region is configured so as to reduce a magnitude of stray magnetic fields on the first capture region below a minimum stray threshold when the second magnetic field generator is interrogating the second capture region.

\* \* \* \* \*